(12) United States Patent
Higgins et al.

(10) Patent No.: US 8,949,075 B2
(45) Date of Patent: Feb. 3, 2015

(54) BLIND LOGGER DYNAMIC CALLER

(75) Inventors: Timothy Alan Higgins, Fort Collins, CO (US); Narasimhachar Sortur, Fort Collins, CO (US)

(73) Assignee: Hach Company, Loveland, CO (US)

( * ) Notice: Subject to any disclaimer, the term of this patent is extended or adjusted under 35 U.S.C. 154(b) by 426 days.

(21) Appl. No.: 13/154,531

(22) Filed: Jun. 7, 2011

(65) Prior Publication Data

US 2011/0307221 A1    Dec. 15, 2011

Related U.S. Application Data

(60) Provisional application No. 61/397,362, filed on Jun. 10, 2010.

(51) Int. Cl.
| | |
|---|---|
| G06F 19/00 | (2011.01) |
| G01F 23/00 | (2006.01) |
| G01F 1/00 | (2006.01) |
| G06F 17/40 | (2006.01) |
| G01F 15/06 | (2006.01) |

(52) U.S. Cl.
CPC ..................... *G01F 15/063* (2013.01)
USPC .......................................... 702/187; 702/188

(58) Field of Classification Search
CPC ......... G06F 17/40; G06F 15/177; G01F 1/00; G01F 23/00; G01D 1/00; G08C 19/16
USPC ...................... 702/187, 188, 45, 55
See application file for complete search history.

(56) References Cited

U.S. PATENT DOCUMENTS

| | | | |
|---|---|---|---|
| 4,343,191 A * | 8/1982 | Cairenius | 73/861.05 |
| 4,650,562 A | 3/1987 | Harman, III et al. | |
| 5,315,880 A | 5/1994 | Bailey | |
| 5,506,791 A | 4/1996 | Hungerford et al. | |
| 5,544,531 A | 8/1996 | Heckman | |
| 5,633,809 A | 5/1997 | Wissenbach et al. | |
| 5,644,088 A | 7/1997 | Heckman | |
| 5,691,914 A | 11/1997 | Randolph | |
| 5,811,688 A | 9/1998 | Marsh et al. | |
| 6,208,943 B1 | 3/2001 | Randolph et al. | |
| 6,917,891 B2 | 7/2005 | Rothfuss et al. | |
| 7,647,400 B2 | 1/2010 | Abbott et al. | |
| 2004/0172210 A1 | 9/2004 | Rothfuss et al. | |
| 2007/0242688 A1 | 10/2007 | McFarland | |
| 2008/0043983 A1 | 2/2008 | Waalkes et al. | |
| 2008/0155064 A1* | 6/2008 | Kosuge et al. | 709/219 |

(Continued)

FOREIGN PATENT DOCUMENTS

| | | |
|---|---|---|
| JP | 2005-003491 A | 1/2005 |
| JP | 2007-334465 A | 12/2007 |
| KR | 10-0364917 B1 | 5/2000 |

OTHER PUBLICATIONS

Search Report and Written Opinion received in Application No. PCT/IB2011/052479 dated Jan. 19, 2012.

*Primary Examiner* — Eliseo Ramos Feliciano
*Assistant Examiner* — Ruihua Zhang
(74) *Attorney, Agent, or Firm* — Ference & Associates LLC

(57) ABSTRACT

Described is an apparatus and method for remotely controlling the call interval of an environmental instrument for a water quality monitoring apparatus based on environmental data obtained by one or more environmental instruments.

33 Claims, 5 Drawing Sheets

(56) References Cited

U.S. PATENT DOCUMENTS

| | | | |
|---|---|---|---|
| 2009/0109021 A1* | 4/2009 | Paoletti et al. | 340/540 |
| 2010/0132803 A1* | 6/2010 | Fima | 137/79 |
| 2010/0204924 A1* | 8/2010 | Wolfe et al. | 702/25 |
| 2011/0066297 A1* | 3/2011 | Saberi et al. | 700/287 |
| 2011/0115640 A1* | 5/2011 | Jiang et al. | 340/870.01 |
| 2011/0209067 A1* | 8/2011 | Bogess et al. | 715/736 |

* cited by examiner

BLIND LOGGER DYNAMIC CALLER

CROSS-REFERENCE TO RELATED APPLICATIONS

This application claims priority of U.S. Provisional Application No. 61/397,362, entitled "New Blind Logger Dynamic Caller" filed Jun. 10, 2010, the entire contents and disclosure of which are incorporated herein by reference.

FIELD OF THE INVENTION

The present invention relates to an apparatus and method for remotely monitoring water quality.

BACKGROUND

Systems for monitoring the characteristics of water sources are critical to many industries. For example, such monitoring is required for many regulatory agencies such as the EPA and FDA. Often, water sources that are of interest are located in remote locations that are difficult to access by humans. Therefore, water monitoring is done by means of automated collection of samples by a sampler device. Automated remote sampling of water sources allows for sampling of water sources at varying times and locations. Traditionally, the remotely located samplers are delivered to their installed site with a predetermined schedule for monitoring. For example, in one such water quality monitoring system a sampler may be installed at a remote Mississippi tributary with a preset sampling schedule of one sample every 12 hours. But there are several drawbacks to systems of this type. For example, one drawback is that the preset sampling schedule may need to be modified. Also, accessing the remote site may be difficult and expensive. In addition, the person performing the installation is often a contractor to the environmental engineer and, therefore, does not have the authority to make on-site modifications to the sampling parameters of the monitoring system.

SUMMARY

According to a first broad aspect of the present invention, there is provided an apparatus comprising: one or more environmental instruments for collecting water quality data, a communication server for communicating with the environmental instruments, a call interval modifying module for changing a call interval for each environmental instrument of the one or more environmental instruments based on the collected water quality data and an environmental condition threshold value for the environmental instrument, and a web server for displaying on a visual display device the status of the one or more environmental instruments and/or the collected water quality data to a user, wherein the web server is in communication with the communication server and the visual display device.

According to a second broad aspect of the present invention, there is provided a method comprising the following steps: (a) providing water quality data collected by one or more environmental instruments, and (b) changing a call interval for a selected environmental instrument of the one or more environmental instruments based on the collected water quality data.

According to a third broad aspect of the present invention, there is provided an apparatus comprising: one or more environmental instruments for collecting water quality data, a communication server for communicating with the environmental instruments, an instrument status-based call modifying module for changing a call interval for each of the one or more environmental instruments based on an environmental instrument status and an environmental instrument status threshold value for the environmental instrument, and a web server for displaying on a visual display device the status of the one or more environmental instruments and/or the collected water quality data to a user, wherein the web server is in communication with the communication server and the visual display device.

According to a fourth broad aspect of the present invention, there is provided a method comprising the following steps: (a) one or more environmental instruments sending collected water quality data to a communication server at a frequency based on a first call interval, and (b) changing a selected environmental instrument of the one or more environmental instruments from a first call interval to a second call interval based on a status of the selected environmental instrument, wherein after step (b) the selected environmental instrument sends the collected water quality data to the communication server at a frequency based on the second call interval.

BRIEF DESCRIPTION OF THE DRAWINGS

The accompanying drawings illustrate exemplary embodiments of the invention, and, together with the general description given above and the detailed description given below, serve to explain the features of the invention. The figures are not necessarily to scale, and some features may be exaggerated to show details of particular components. Therefore, specific details disclosed herein are not to be interpreted as limiting, but merely as a basis for the claims and as a representative basis for teaching one skilled in the art to variously employ the present invention. As a result, the invention is not limited to the specific examples described below, but only by the claims and their equivalents.

DETAILED DESCRIPTION

Definitions

Figure 1:
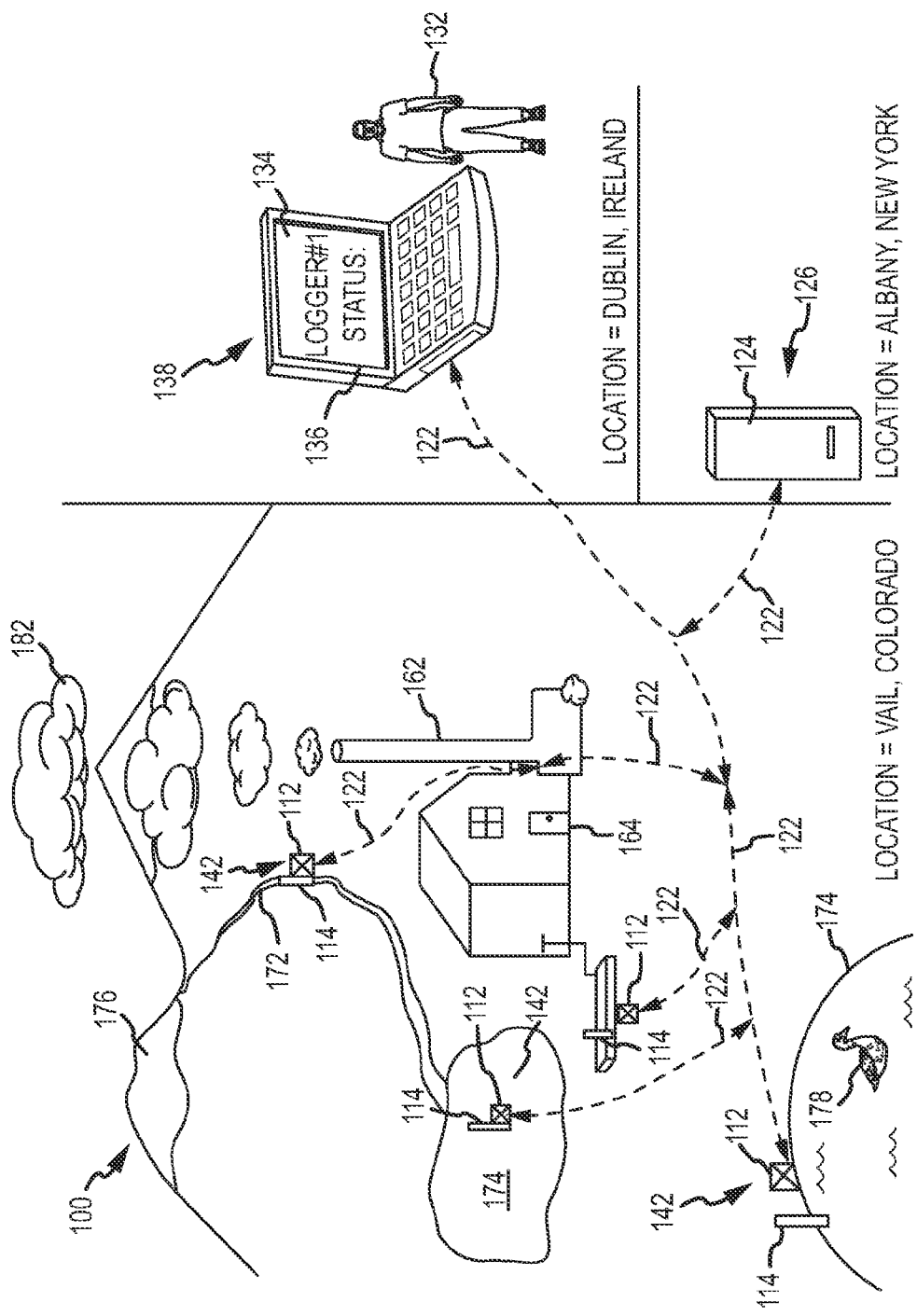
FIG. 1 is a schematic diagram illustrating a water quality monitoring apparatus according to one embodiment of the present invention.

Where the definition of a term departs from the commonly used meaning of the term, applicant intends to utilize the definition provided below, unless specifically indicated.

For purposes of the present invention, it should be noted that the singular forms, "a," "an," and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc. are used merely for convenience in describing the various embodiments of the present invention. The embodiments of the present invention may be oriented in various ways. For example, the diagrams, apparatuses, etc. shown in the drawing figures may be flipped over, rotated by 90° in any direction, reversed, etc. For example, rows and/or columns may be oriented in any direction.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "analysis report" refers to any organized presentation of data, raw data or historical data, manipulated data, observational data, information, analysis result, etc., based on data obtained or collected from one or more sensors and that is generated or manipulated by an analyzer on an environmental instrument and/or server. An analysis report may be prepared for any intended recipient, such as an elected official, manager or operator of a water treatment system, customer, member of the public, etc. According to some embodiments of the present invention, an "analysis report" may be a submission to a regulatory and/or law enforcement agency in any required format.

For purposes of the present invention, the term "analysis result" refers to any information, value, relationship, product, etc., created by aggregation, calculation, algorithm, analysis, manipulation, etc., of data or information obtained or collected from one or more sensors as performed by an analyzer on the environmental instrument and/or the server of the present remote water quality monitoring system. For example, an "analysis result" may include observational data analyzed, manipulated, etc., by an environmental instrument.

For purposes of the present invention, the term "analyzer" refers to a portion of an environmental instrument, such as a sampler or logger, or a portion of a server in which may be stored one or more software program(s) or other routine(s), firmware and/or hardware, which may analyze, manipulate, etc., data such as raw data, observational data, historical data or any other information obtained from one or more environmental instruments. According to some embodiments of the present invention, an analyzer may analyze or manipulate the data to generate the output. The analyzer may comprise a source code or a software program. According to some embodiments of the present invention, the analyzer may compare the data continuously, in real-time, at periodic or selected intervals, on condition or on demand by a user. According to some embodiments of the present invention, the output may comprise one or more of the following: data, alarm, analysis result or analysis report.

For purposes of the present invention, the term "call interval" refers to the frequency at which an environmental instrument initiates a connection to the communication server, i.e., communicates with the communication server, at which point the server transfers data to/from the environmental instrument. Depending on the situation, the call interval may always be a fixed amount of time such as 30 minutes, 1 hour, etc. after the previous call is made by the environmental instrument to the communication server. Alternatively, the call interval can refer to a particular set of times at which the environmental instrument calls, such as on the hour, ten (10) minutes after the hour, etc.

For purposes of the present invention, the term "call interval modifying module" refers to hardware and/or software that allow a user and/or an environmental instrument to change the call interval for the environmental instrument based on collected environmental data. A call interval modifying module may be stored in an environmental instrument and/or a server. A call interval modifying module may be part of an environmental instrument, a server, a web-enabled application, etc.

For purposes of the present invention, the term "communication server" refers to a server in communication with one or more environmental instruments. A communication server receives data from the one or more environmental instruments. A communications server also sends data and/or instructions to the one or more environmental instruments. Some data and/or instructions sent by a communication server to an environmental instrument may result in an environmental instrument changing its call interval.

For purposes of the present invention, the term "data" refers to any information, reading, measurement, value, etc., ultimately obtained from one or more sensors or derived from such data. The term "data" includes any data or information, including raw data obtained directly from one or more sensors without manipulation, historical data earlier obtained from one or more sensors or entered or derived from data obtained at an earlier point or period in time, and analyzed or manipulated data, such as data or information manipulated, analyzed, etc., by an analyzer. The term "data" may include, for example, an analysis result or observational data.

For purposes of the present invention, the term "database" refers to a device or apparatus of the present remote water quality monitoring system used to store data, raw data, historical data, manipulated data and/or information in a logical or ordered arrangement or configuration. The database may be either part of the server or separate from the server, albeit connected to or in communication with the server.

For purposes of the present invention, the term "distant" in reference to a server and/or server database refers to the server and/or server database being physically separated from an environmental instrument or remote user. The term "distant" may refer to a server and/or server database that is connected with or linked to one or more environmental instruments and one or more remote users only via a wireless communication system.

For purposes of the present invention, the term "electronic control system" refers to a portion of a water treatment system that may control the operation of equipment and operation of a water treatment system. According to some embodiments of the present invention, a server of the present invention may access or collect data from one or more sensors via an electronic control system. An electronic control system may include an in-house supervisory control and data acquisition system (SCADA) or a programmable logic controller (PLC).

For purposes of the present invention, the term "environmental condition threshold value" refers to an environmental data value that is used to determine if an environmental instrument should be switched from a primary call interval to a secondary call interval and/or from a secondary call interval to a primary call interval. The environmental condition threshold value is a value that environmental data must be less than, less than or equal to, greater than or greater than or equal to, in order cause a change in the call interval for the environmental instrument, depending on the particular situation. For example, if there is a concern about too little water flow, an environmental instrument may be switched from a primary call interval to a secondary call interval if the measured water level is less than a threshold water level value. The environmental instrument may be switched back to the primary call interval if the measured water equals or exceeds the threshold water level. If there is a concern about too much water flow, an environmental instrument may be switched from a primary call interval to a secondary call interval if the measured water level is greater than a threshold water level value. The environmental instrument may be switched back to the primary call interval if the measured water is less than or equal to the threshold water level.

For purposes of the present invention, the term "environmental data" refers to data obtained by a sensor that relates to the environment or changes to the environment of a location at which a sensor is located.

For purposes of the present invention, the term "environmental instrument" refers to a sampler, a logger, or a sensor or any other device that is used in the process of monitoring water.

For purposes of the present invention, the term "environmental instrument status" refers to any condition associated with the environmental instrument such as an environmental instrument's power level, temperature, age, usage history, etc.

For purposes of the present invention, the term "instrument status-based call modifying module" refers to hardware and/or software that allows a user and/or an environmental instrument to change the call interval for the environmental instrument based on the status of an environmental instrument. An instrument status-based call modifying module may be stored in an environmental instrument and/or a server. An instrument status-based call modifying module may be part of an environmental instrument, a server, a web-enabled application, etc. environmental instruments based on an environmental instrument status and an environmental instrument status threshold value for each environmental instrument. An instrument status-based call modifying module may be part of a call interval modifying module or may be a separate module.

For purposes of the present invention, the term "hardware and/or software" refers to functions that may be performed by digital software, digital hardware or a combination of both digital hardware and digital software. For example, a "program" may be a software program, a program that is part of the digital hardware of a computer or environmental instrument, or a combination of both digital hardware and digital software.

For purposes of the present invention, the term "instrument condition threshold value" refers to an environmental instrument status value that is used to determine if an environmental instrument should be switched from a primary call interval to a secondary call interval and/or from a secondary call interval to a primary call interval. The instrument condition threshold value is a value that a condition of the environmental instrument must be less than, less than or equal to, greater than or greater than or equal to in order to cause a change in the call interval for the environmental instrument, depending on the particular situation. For example, if a battery-powered environmental instrument has a power value that falls below a power threshold value for the environmental instrument, the environmental instrument may be switched from a primary interval to a secondary interval that calls in to a communication server less frequently to prolong the battery life of the environmental instrument.

For purposes of the present invention, the term "interactive visual display device" refers to a visual display device that a user may interact with by means of an input device. The input device may be a touchscreen of the visual display device, a touchpad, a mouse, a trackball, a keyboard, etc. Examples of interactive visual display devices include a computer with a monitor, a laptop computer, a tablet computer, a cell phone, a smartphone, etc.

For purposes of the present invention, the term "logger" or "data logger" refers to a device that records data. An example of a logger is a water flow logger that records the water flow of a water source.

For purposes of the present invention, the term "logging interval" refers to the frequency at which a logger records data. A logging interval for a logger may be different than the call interval for a logger. For example, a logger may log data several times between each call interval. By sending data less frequently, i.e., having a longer call interval, the logger may conserve power.

For purposes of the present invention, the term "mode of communication" and the term "communication link" refer to any suitable technology or device known and available in the art for communicating between two or more devices. A mode of communication may be achieved or carried out through any suitable medium, such as any wired or wireless connections as well as any protocols, including, but not limited to: the Internet; GMR (Geo-Mobile Radio); TCP/IP; MODBUS RTU, MODBUS ASCII, and MODBUS TCP; XML; Ethernet; file transfer protocol (FTP); Bluetooth®; ZigBee; e-mail, such as SMTP; cellular modems; cellular phone networks, such as CDMA and TDMA; radio signals or remote terminal units (RTU) coupled to radio frequency transmitters; satellite transmission; SDI-12; existing telephone or communication networks or wiring; a standard Public Switched Telephone Network (PSTN); dial-up using landline or telephone; a wireless network such as Wi-Fi; a wide area network (WAN); a wireless local area network (WLAN); a local area network (LAN) or a metropolitan area network (MAN); a cable Internet connection; short message system (SMS); dial-up modem; a point-to-point link; global system for mobile communications (GSM, 3GSM), general packet radio services (GPRS), evolution-data optimized (EV-DO), enhanced data rates for GSM evolution (EDGE), digital enhanced cordless telecommunications (DECT), integrated digital enhanced network (iDEN), universal mobile telecommunications systems (UMTS) or advanced mobile phone systems (AMPS); or any other means for communicating between two or more devices known to those skilled in the art. The exact mode of communication may vary depending on the circumstances. According to some embodiments of the present invention, a communication link may be used to transmit and/or receive communications between two or more devices continuously, in real-time, at periodic or selected intervals, on condition or on demand by a user or by one or more of the two or more devices.

For purposes of the present invention, the term "observational data" refers to data or information that has been analyzed, manipulated, etc., by the environmental instrument, such as by an analyzer on the environmental instrument, from raw data or information obtained from one or more sensors prior to being transmitted to a server and/or server database.

For purposes of the present invention, the term "output" refers to any product, publication, submission, uploaded content, etc., including any information, data, analysis result, analysis report, etc., that may be communicated from the server of the present remote water quality monitoring system to a remote viewing device in a format suitable for display by the remote viewing device to a user.

For purposes of the present invention, the term "output device" refers to any device or apparatus known in the art that may be used by a user to view or that makes a user aware of an output of the water quality monitoring system, such as, for example, personal computers or terminals, servers, etc., as well as a variety of handheld personal communications equipment, such as cell phones, pagers, PDAs, BlackBerrys®, Palm® devices, iPhones®, etc.

For purposes of the present invention, the term "processor" refers to a single processing device or a group of inter-operational processing devices. Some examples of processors are computers, integrated circuits, logic circuitry, etc.

For purposes of the present invention, the term "remotely located" and the term "remote" refer to instruments being physically isolated except for direct collaboration with each other or indirect interaction through a website such as FSDATA™.

For purposes of the present invention, the term "remote user" refers to a user that is remote from one or more environmental instruments of a water quality monitoring system according to an embodiment of the present invention.

For purposes of the present invention, the term "remote water quality monitoring system" refers to a system for remotely monitoring the operation and equipment of a remotely located water treatment system or the water quality in, toward or from a remotely located water treatment system using sensors to collect data that is transmitted to a server for analysis, manipulation and communication to a remote viewing device for a user.

For purposes of the present invention, the term "sampler" refers to a device that draws predefined liquid volumes based on a set of rules. The set of rules may be preset for the sampler or defined in a sample program for the sampler by a user. Examples of samplers include Hach sd900™, American Sigma 900Max™, etc.

For purposes of the present invention, the term "sensor" and the term "water quality sensor" refer to a device, probe or apparatus for the detection or measurement of parameters or values relevant to water quality, such as values for water flow including water level, flow velocity, etc. The term "sensor" may refer to a device, probe or apparatus connected to an environmental instrument, such as a logger.

For purposes of the present invention, the term "server" refers to one or more computers with which environmental instruments and remote visual display devices communicate. The server computer may collect, assemble, aggregate, manipulate or analyze data from one or more sensors of the present remote water quality monitoring system prior to the data being transmitted to the server of the present remote water quality monitoring system. The "server" may be any computer able to (1) at least temporarily store, collect, assemble, aggregate, etc., data from one or more sensors and (2) transmit data or information to a server (or a server database associated with the server) via a mode of communication. Thus, a "server" may contain or include (1) one or more memory device(s) to store, collect, assemble, aggregate, etc., the data at least temporarily, (2) one or more ports or inputs for receiving data or information either directly or indirectly from one or more sensors, and (3) one or more transmission interface(s) to transmit data or information to a server. Also, a "server" may have the ability to process, manipulate, analyze, etc., the data obtained from the one or more sensors, such as by an analyzer or software located on the environmental instrument, prior to transmission of data or information to the server and/or server database. A "server" may be a web or Internet server. The "server" may further include a database and/or an analyzer.

For purposes of the present invention, the term "server database" refers to a device or apparatus of the present remote water quality monitoring system used to store data, raw data, historical data, manipulated data and/or information, such as in a logical or ordered arrangement or configuration. The server database may be part of the server or separate, albeit connected to or in communication with the server. As such, the "server database" is physically separated, i.e., at a remote or distant location, from the location of the environmental instruments and the remote users of a remote water quality monitoring system.

For purposes of the present invention, the term "set of environmental instruments" refers to the environmental instrument(s) at a particular location. A set of environmental instruments may comprise a single sampler, logger or sensor or may comprise a combination of one or more samplers, one or more loggers and/or one or more sensors.

For purposes of the present invention, the term "transmission interface" refers to a portion of an environmental instrument, electronic control system and/or one or more sensors of a remote water quality monitoring system that is capable of transmitting data or information to a server via any suitable wireless mode of communication.

For purposes of the present invention, the terms "treat," "treated," "treating," "treatment," and the like shall refer to any process, treatment, generation, production, discharge or other operation that may be performed by a water treatment system on, or in relation to, the water in the water treatment system.

For purposes of the present invention, the term "user" refers to a person, entity or agency that views data, information, analysis results or analysis reports communicated from the server to the remote viewing device of the present remote water quality monitoring system.

For purposes of the present invention, the terms "visual display device" and "visual display apparatus" include any type of visual display device or apparatus such as a CRT monitor, LCD screen, LEDs, projected display, printer for printing out an image such as a picture and/or text, etc. A visual display device may be a part of another device such as a computer monitor, television, projector, cell phone, smartphone, laptop computer, tablet computer, handheld music and/or video player, personal data assistant (PDA), handheld game player, head-mounted display, heads-up display (HUD), global positioning system (GPS) receiver, an automotive navigation system, a dashboard, watch, microwave oven, automated teller machine (ATM), etc. A visual display device is one type of output device.

For purposes of the present invention, the term "water" refers to any type of water found in nature, contaminated or uncontaminated by pollutants, and water or any fluid that may be processed, treated, generated, produced, discharged, etc., by a water treatment system. For example, the term "water" may refer to wastewater collected by a wastewater collection system or to water being treated or processed by a water treatment facility for the distribution of potable drinking water to the public, or the term "water" may refer to effluent from an industrial plant, or sewage or wastewater processed or treated by a central wastewater treatment plant (WWTP). Thus, "water" may include any number of pollutants, solutes, sediments, suspensions, organic matter, etc., as the case may be.

For purposes of the present invention, the term "water flow logger" refers to a logger that records water flow of a water source. A water flow logger may be used to determine the rate of flow, level or velocity in a natural water flow such as a creek, stream, river, etc., or water flow in a man-made conduit such as a canal, pipe, weir, flume, sewer, etc.

For purposes of the present invention, the term "water quality" refers to any characteristic of water, including such characteristics as flow, velocity, level, conductivity, potability, turbidity, pH, dissolved solids, concentration of various impurities, concentration of various metals, concentrations of various ions, etc., for a water source or a water stream.

For purposes of the present invention, the term "water source" refers to any source of water, either natural or man-made. Examples of water sources include oceans, gulfs, bays, lakes, rivers, streams, creeks, reservoirs, sewers, water tanks, water pipes, effluent from industrial plants, wastewater collection systems, wastewater treatment plants, etc.

For purposes of the present invention, the term "water stream" refers to any flow of water or waterway. Examples of water streams include natural flows of water such as a creek, stream, river, etc., or flows of water in a man-made conduit such as a canal, pipe, weir, flume, sewer, channel, etc.

For purposes of the present invention, the term "water system" refers to a water stream, a water source or combination of water stream(s) and/or water source(s). Examples of water systems include wastewater collection systems, sewer systems, wastewater treatment systems, etc.

For purposes of the present invention, the term "water treatment core facility" refers to a central facility that processes, treats, generates, etc., water in contrast to a broader collection or distribution system, such as a central wastewater treatment plant, for the processing or treatment of wastewater, or a water treatment facility, such as a facility for the generation of potable drinking water.

For purposes of the present invention, the term "water treatment system" refers to any system designed or used to process, treat or generate water or a water-based product for a particular application. A "water treatment system" may be used to generate water having a predetermined, desired, or preferred set of characteristics, qualities or properties, such as purity, etc. For example, a "water treatment system" may include a water treatment facility for generating and distributing potable drinking water for the public, a system designed to generate water for a manufacturing process, etc. In the case of a water treatment facility for generating potable drinking water, the water treatment system may further include a distribution system for distributing potable drinking water to the public. A "water treatment system" may also be any system used to process or treat a water-based substance into a product that may be discharged into the environment, such as a central WWTP, etc. In the case of a WWTP, the water treatment system may further include a collection system for collecting wastewater and funneling it into the central WWTP. Water treatment systems may include public or municipal systems or private systems dedicated to an industry, factory or particular real estate development. For example, a water treatment system may include any system, plant or facility that uses equipment based on advanced separation, filtration, dialysis, ion exchange processes or any other basis, technology or mechanism for processing, treating, detecting, purifying, isolating, separating, etc., water according to relevant parameters.

For purposes of the present invention, the term "web-enabled application" refers to an application that is run from the Web or Internet. A web-enabled application may be run within a web browser, may run on a web server, may output HTML for display on the Web, may launch a web browser to retrieve specific web page, etc.

For purposes of the present invention, the term "web server" refers to the conventional meaning of those terms, i.e., a computer that helps deliver content to another computer, a user, a visual display device, etc. that can be accessed through the Internet. In one embodiment of the present invention, a water quality monitoring system includes a communication server to interact with the remote loggers and samplers, a web server to display a user interface to an Internet browser that is display on a visual display device, and a database server that does not have external access.

DESCRIPTION

Water quality monitoring systems often include sensors that measure the concentration of ions in the solution. The solution can be aqueous or organic in nature. One commonly monitored ion is the hydronium ion; however, any cation or anion can be of importance to a water quality monitoring system.

The quality of water is highly influenced by the concentration of hydronium ions ($H_3O^+$, or $H^+$), or pH, of the reaction environment. The pH of a solution is also often referred to as the acidity of the fluid being tested. By definition, pH=−log [$H_3O^+$], or the negative log of the molar concentration of hydronium ions. On the pH scale, a very acidic solution has a low pH value, such as zero or one, corresponding to a large concentration of hydrogen ions ($H^+$). In contrast, a very basic solution has a high pH value, corresponding to a very small number of hydrogen ions (or to a correspondingly large number of $OH^-$ ions). A neutral solution, such as substantially pure water, has a pH value of about seven.

The presence of the correct concentration of acid in a solution can induce many forms of catalysis, such as, but not limited to, acetal formation, acetal hydrolysis, dehydration of alcohols, amide hydrolysis, epoxide ring opening, ester hydrolysis, esterification, ether formation and glycoside formation. The correct pH concentration can also include catalysis of hydration including, but not limited to, alkenes, alkynes, nitriles, nucleophilic acyl substitution and nucleophilic addition to aldehydes and ketones.

The pH of potable drinking water is a required reporting parameter of many governments, and effluent water pH ranges are strictly controlled. For example, in the United States the Environmental Protection Agency sets specific ranges for potable water discharge; if the water pH is outside the range, the water can be unsafe for human and animal consumption.

Water is also required for steam generation in nuclear reactors. The boilers of these nuclear reactors operate at extremely high temperatures that require a very high quality of water. It is critical that the process system is monitored properly to avoid expensive boiler cleanings and the associated downtime. Such systems may also include the need to monitor hazardous boiler chemicals, such as hydrazine, requiring highly qualified personnel. These examples highlight the importance of monitoring water supplies to not only ensure sufficient water quality, but also to avert costly equipment repair or replacement.

Water quality is also important for many manufacturing processes. For example, the manufacturing of semiconductors requires an ultra-pure water quality. Again, it is critical that the water supply be monitored properly to avoid latent defects in the manufacturing of products, such as semiconductors.

As yet another example, monitoring water quality is also important to avoid or lessen the consequences of equipment failure or deliberate tampering (such as by terrorist act) in contaminating the water supply. Adequate monitoring may help to catch any such contamination of the water supply to avoid harm and ensure that appropriate action is taken.

Embodiments of the present invention relate to an environmental sensor data logger that employs a dynamic call interval that allows a user, a remote server or the logger itself to modify the frequency of calls into the remote server based upon user instructions, environmental conditions or a combination of both.

Various types of methods for dynamically exchanging information have been described. For example, U.S. Pat. No. 7,647,400 to Abbot et al., entitled "Dynamically exchanging computer user's context," issued Jan. 12, 2010, describes dynamically exchanging computer user's context. Techniques for providing information about a current state modeled with multiple attributes are described. The providing of information can include receiving from a first source an indication of an ability to supply values for one of the state attributes of the modeled current state, and supplying to a client a value for the one attribute received from the first source. After supplying the value(s), the providing of information can include receiving from the first source an indication of a value supplying inability for the one attribute and supplying a value for the attribute received from the other source. But the Abbot et al. patent does not describe an environmental logging device with a dynamic reporting and control interval. The entire contents and disclosure of Abbot et al. are incorporated herein by reference.

Logging data from a dynamic liquid is critical to many industries and water types. It is a required reporting parameter for many regulatory agencies such as the EPA and FDA. For example, U.S. Patent Application No. 2007/0242688 to McFarland, entitled "Dynamic value reporting for wireless automated systems," published Oct. 18, 2007, describes a dynamic value reporting for wireless automated systems. The wireless automation device monitors a condition and wirelessly reports an event over an automation network in response to detecting a change in the condition. The condition is sampled at a variable periodic interval, and the event is reported during intervals when a change in the condition is determined. The change may be determined according to detecting a value for the condition outside a variable range. The change may also be determined according to detecting differences in the value from values detected in prior intervals. The range and the periodic interval may vary according to an analysis of multiple samples of the condition. But McFarland does not describe an environmental logging device with a dynamic reporting and control interval. The entire contents and disclosure of McFarland are incorporated herein by reference.

U.S. Patent Application No. 2008/0043983 to Waalkes et al., entitled "System and method for managing a dynamic call flow during automated call processing," published Feb. 21, 2008 describes a system and method for managing a dynamic call flow during automated processing. Calls from a plurality of callers into a call center are accommodated. The call flow of each call session is dynamically adjusted by modifying parameters for one or more of the caller characteristics and physical conditions. The caller characteristics, physical conditions and parameters are stored in a database. But Waalkes does not describe an environmental logging device with a dynamic reporting and control interval. The entire contents and disclosure of Waalkes et al. are incorporated herein by reference.

U.S. Pat. No. 6,917,891 to Rothfuss et al., entitled "Systems and methods for diagnosing and predicting fluid flow systems using sensors," issued Jul. 12, 2005, describes a fluid flow system for continuously monitoring the flow of fluid in a fluid flow that includes a conduit with an upstream side and a downstream side and sensors with fluid flow elements. Rothfuss et al. also describes a method for analyzing the operation of a fluid flow system by determining whether the fluid flow subsystem of the main system is operating properly, inputting a sensor reading of the parameter in the fluid flow of the main system and outputting an error indication of the main system. But Rothfuss et al. does not describe an environmental logging device with a dynamic reporting and control interval. The entire contents and disclosure of Rothfuss et al. are incorporated herein by reference.

The publication "Hach Company Sigma 930T Literature No. 3467," the entire contents and disclosure of which are incorporated herein by reference, describes a remote communications flow meter. The Sigma 930T is a remote flow monitoring apparatus that monitors various parameters of a dynamic water source. The apparatus can continuously monitor data in real-time and provides for managing user-set alarms, level measurement, and Doppler-based flow measurement. The Sigma 930T logs information within the guidelines preset by the user. Applications include, but are not limited to, permanent collection system monitoring, long-term flow monitoring, sanitary sewer evaluation studies, and CSO and SSO studies and monitoring. But this publication does not describe an environmental logging device with a dynamic reporting and control interval.

Accordingly, there has not heretofore been described an apparatus and method for an environmental logging device with a dynamic reporting and control interval having the features and advantages provided by the present invention.

In one embodiment, the present invention provides a water monitoring apparatus that comprises environmental instruments, such as loggers and/or samplers, in communication with one or more water quality sensors and in communication with one or more remotely located servers. The remotely located servers are in communication with one or more user interfaces via a web-enabled browser. The environmental instrument and/or the server and/or the user can change the call interval for the environmental instrument in a response to a change in sensed conditions.

In one embodiment, the present invention provides an environmental instrument in which the call interval for the environmental instrument is changed based upon an analysis of the data by a server and/or by a user.

FIGS. 1, 2, 3 and 4 and the following detailed description of the present invention are disclosed herein; however, it is to be understood that the disclosed embodiments are merely exemplary of the invention that may be embodied in various forms. The figures are not necessarily to scale, and some features may be exaggerated to show details of particular components. Therefore, specific details disclosed herein are not to be interpreted as limiting but merely as a basis for the claims and as a representative basis for teaching one skilled in the art to variously employ the present invention. As a result, the invention is not limited to the specific examples described below, but only by the claims and their equivalents.

FIG. 1 shows a water quality monitoring system 100 according to one embodiment of the present invention that includes one or more remote loggers 112 and one or more remote sensors 114. In water quality monitoring system 100 data is wirelessly transmitted via wireless bidirectional communication links 122. For example, data is transmitted in both directions via respective wireless bidirectional communication links 122 between loggers 112 and server 124 at a remote location 126, i.e., Albany, N.Y. Also, data is transmitted in both directions via one of wireless bidirectional communication links 122 between server 124 and a remote user 132, such as an engineer, thereby allowing for a visual display of the data on a web-enabled browser 134 on an interactive visual display device 136, i.e., a laptop computer at a remote location 138, i.e., Dublin, Ireland.

Each logger 112 collects data from different sensors 114 regularly based on the user settings. To transfer data to server 124, logger 112 makes a data call to server 124 at regular intervals via a wireless bidirectional communication link 122 to upload data such as real-time data, an event log, sensor diagnostics information, or any other water quality parameter data at each location 142 detected in the environment at the location. The ability of any number of loggers 112 to call via a wireless bidirectional communication link 122 to server 124 facilitates pushing real-time data available at logger 112 to server 124 for analysis, review or reporting to the user 132 via web-enabled browser 134. Each logger 112 provides the capability for user 132 to set a channel to trigger an alarm to start taking samples more often at different intervals based on an alarm triggered by an environmental condition, such as a rain event, being detected by one or more sensors 114. As a part of the alarm action, user 132 can set the alarm so that user 132 is notified by SMS, email, or another type of notification method by logger 112 via wireless bidirectional communication link 122 from server 124 (after server 124 has received the alarm from logger 112).

The dynamic calling/logging performed by water quality monitoring system 100 can be performed for any water analysis parameter. By way of example, the water quality parameter of interest may be the detection of water contaminants surrounding an industrial site 162 at a location 164, i.e., Vail, Colo. One or more loggers 112 with their associated one or more sensors 114 are positioned around water sources of interest, such as a stream 172, lake 174, and/or mountain snowcap 176. The water sources may include wildlife 178 that are affected by the water contaminants. Industrial site 162 may or may not discharge contaminants 182 into the environment in any form and/or phase (gas, liquid, solid, super-critical). The dynamic calling/logging of water quality monitoring system 100 allows user 132 to adapt the call interval from any location without having to visit the remote site.

Although at most only one logger and sensor are shown at each location in FIG. 1, there may be two or more samplers, loggers and/or sensors at each location.

Although only one user, visual display device and server are shown in FIG. 1, the water quality monitoring system of the present invention may include multiple users, visual display devices and/or servers. Also, the number of potential different wireless bidirectional communication links between various environmental instruments, servers, visual display devices, etc., may be virtually infinite.

Figure 2:
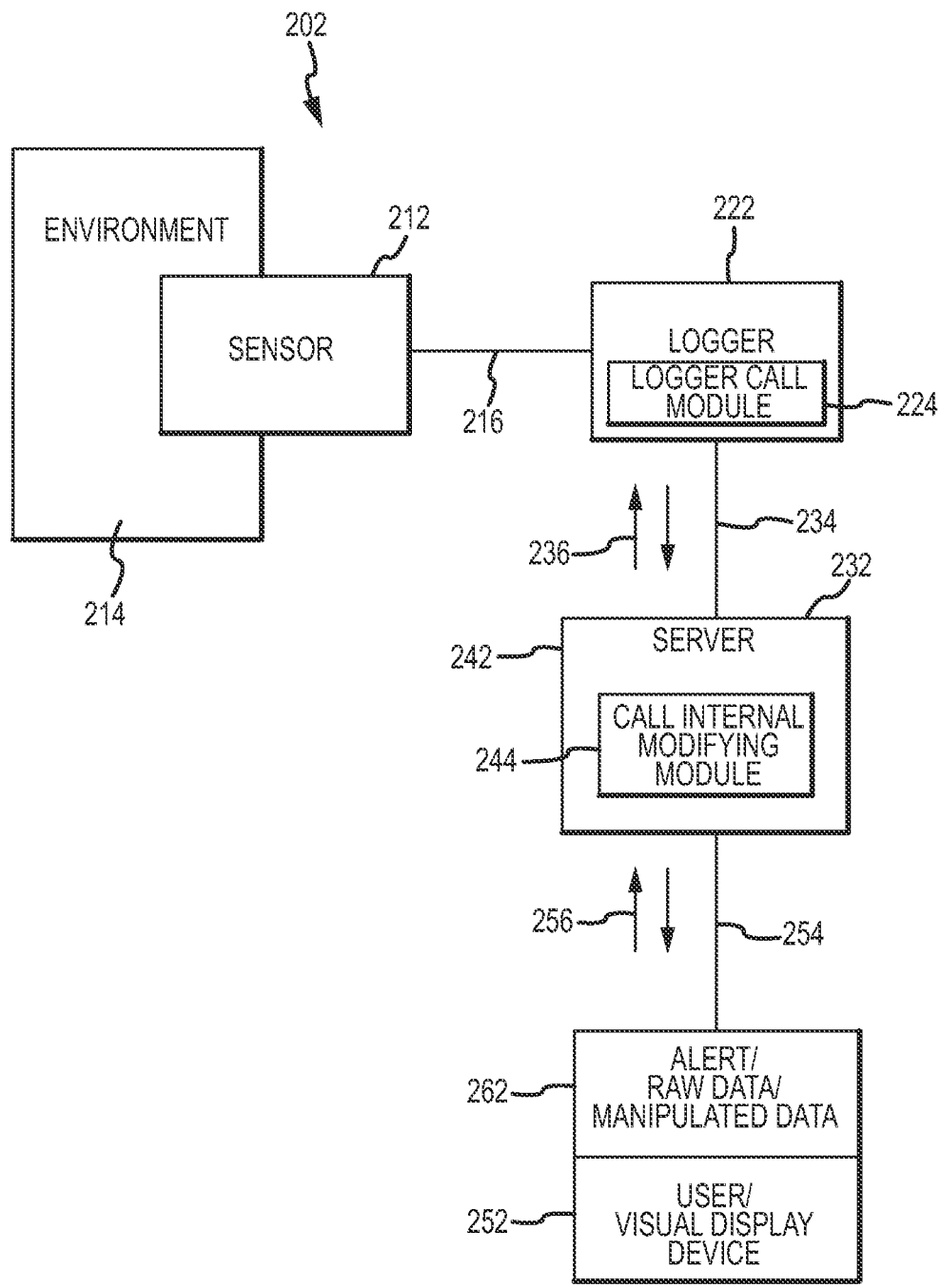
FIG. 2 is a diagram illustrating how the call interval of a logger of the present invention may be modified based on environmental data obtained by a sensor according to one embodiment of the present invention.

FIG. 2 shows an environmental sensor and dynamic call interval method 202 according to one embodiment of the present invention. One or more sensors 212 collect data from one or more environments/locations 214. This data is transmitted via a communication link 216 to a logger 222. The logger 222, via a logger call module 224, determines how often to push this data to a remote server 232 based upon predetermined parameters via a communication link 234 that allows communication in both directions between logger 222 and server 232, as indicated by arrows 236. Remote server 232 includes a call interval modifying module 244. For example, call interval modifying module 242 of remote server 232, upon analysis of the data, can instruct logger 222 to change the call interval of logger 222. In addition, remote server 232 transmits the data to a user/visual display device 252 via a communication link 254 that allows communications in both directions between remote server 232 and user/ visual display device 252 as indicated by arrows 256. That data is displayed on visual display device 252 as displayed data 262 that may be an alert, raw data, manipulated data, etc.

The logger call module of FIG. 2 may be hardware and/or software.

The communication links between the sensor(s) and the logger, between the logger and the remote server and between the remote server and the user may be any type of communication link, i.e., wired, wireless, etc.

Although the call modifying module shown in FIG. 2 is shown as being part of only the server, in other embodiments of the present invention, the call interval modifying module may be part of the logger. In other embodiments of the present invention, one part of the logger interval modifying module may be part of the logger and one part of the call interval modifying module may be part of the server. In yet other embodiments of the present invention, all or part of the logger modifying module may be part of the visual display device.

Although shown as separate devices in FIG. 2, the sensor(s) and logger may be part of the same device.

Figure 3:
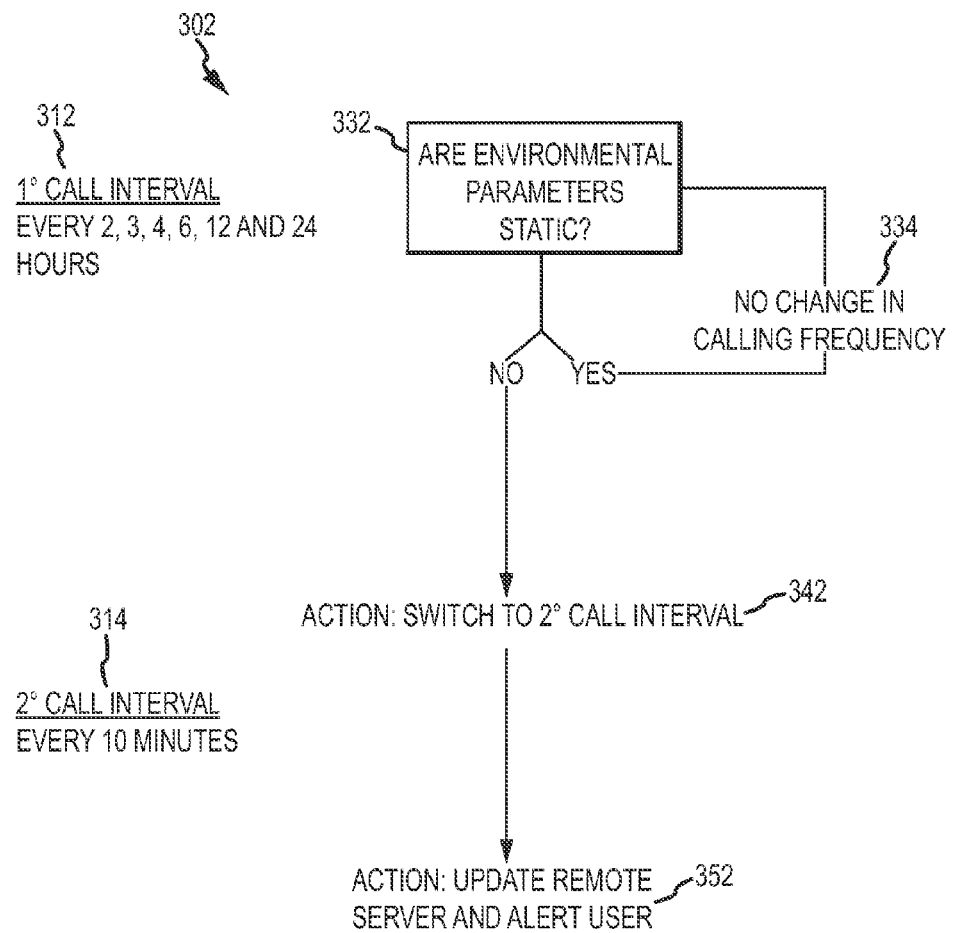
FIG. 3 is a diagram illustrating (1) how the call interval of a logger of the present invention may be changed by a call interval modifying module based on environmental data obtained by a sensor and (2) how a user may be alerted to the change in call interval according to one embodiment of the present invention.

FIG. 3 shows a dynamic call interval decision tree 302 that may be employed by a call interval modifying module according to one embodiment of the present invention in which the primary call interval is different from the secondary call interval based upon a predetermined setting. In FIG. 3, the logger supports two different call intervals to the server, primary call interval 312 and a secondary call interval 314. The logger switches between these two call intervals based on a preset or user set alarm being triggered due to a change of an environmental parameter that is sensed by a sensor in communication with the logger. There may be a number of preset or user set alarms for water quality parameters being monitored such as pH, water flow, water level, flow velocity, etc. These alarms will be sent/displayed to a user when the value for a particular parameter reaches and/or exceeds a threshold value for the parameter or when a value for a particular parameter equals and/or falls below a threshold for the parameter. These alarms may indicate that events of interest such as rain, lack of rain, pollution, etc., have had an effect on the quality of the water source/water flow being monitored.

A primary call interval is the primary period in which the logger has to make a data call to the server, i.e., the regular interval at which the logger makes a data call. This setting can be made to the logger manually on site or remotely by a user. This interval may be any interval setting. For example the interval may be every 5, 6, 10, 12, 15, 30 and 60 minutes or every 2, 3, 4, 6, 12 and 24 hours. The logger, upon expiry of this period, communicates with the server over a communication link. For example, in one embodiment the logger switches on a wireless modem, initializes the modem, makes a connection to the Internet, and creates and connects a TCP Client socket to the server.

A secondary call interval is the secondary period at which the logger has to make a data call to the server upon the triggering of a preset or user set alarm for the secondary call interval. When the any one of the alarms goes active and the secondary call interval is selected as the one of the alarm actions, the logger switches the call interval from primary call interval to the secondary call interval. Then the call interval is switched back to primary call interval after the alarm is cleared.

In FIG. 3, at each primary call interval 312, the logger determines if the environmental parameters are static or have changed at step 332. A change in environmental parameters such as pH, water flow, temperature, etc. can be determined by the logger directly from data obtained from environmental sensors in communication with the logger. If the environmental parameters are determined to be static, step 332 continues to be repeated at the primary call interval as indicated by step 334. If the environmental parameters have been determined to have changed by the logger, then the logger switches the secondary call interval at 342 and updates the remote server and alerts the remote user at step 352.

The ability of the logger to switch between the primary call interval and secondary call interval is called a "dynamic call interval." The use of a dynamic call interval facilitates a logger sending data more frequently to the server and to the user for analysis, review, and control, when a change in environmental conditions is detected.

Although FIG. 3 shows the logger switching between the primary and second call intervals based on the logger determining a change in environmental parameters, in other embodiments of the present invention, the logger may be switched between the primary and secondary interval based on the server and/or user instructing the logger to switch between the primary and secondary call intervals. For example, a user may determine that based on environmental data (from one or more sensors sent by the logger to the server) displayed by the server on a browser on the user's visual display device that there has been a change in the environmental parameters that is indicative of an event of interest happening. The user may then send instructions to the logger through the server to change from the primary call interval to the secondary call interval.

Figure 4:
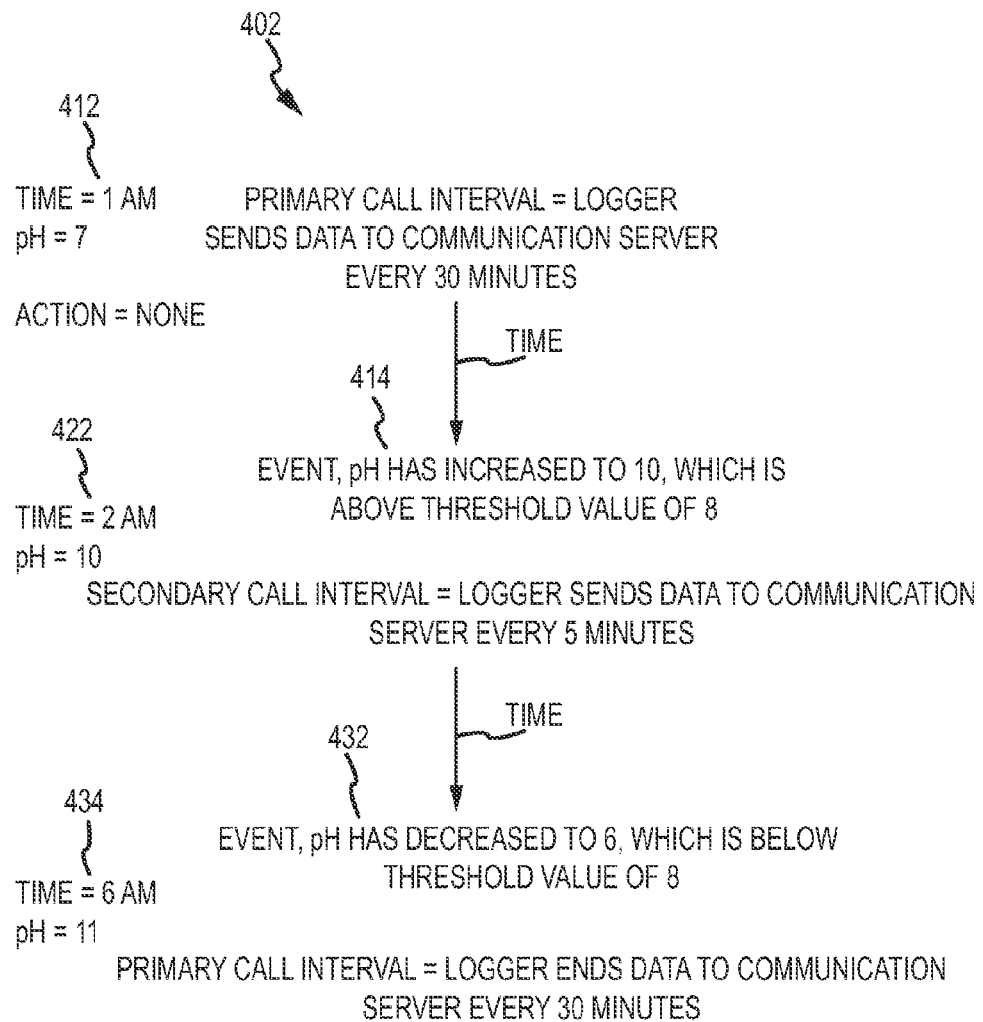
FIG. 4 is a diagram showing a logger changing its call interval based upon changes in environmental conditions according to one embodiment of the present invention.

FIG. 4 shows an example 402 of an environmental logger changing its call interval between a primary call interval and a secondary call interval based upon changes in environmental conditions. At a time 412, i.e., 1:00 AM, the logger has a primary interval of 30 minutes, i.e., the logger sends pH data (obtained from a sensor) to a communication server every 30 minutes. Then an event 414 occurs, i.e., the pH increases to 10 and is detected at time 422, i.e., 2:00 AM, by the environmental sensor, the logger determines that an environmental parameter, i.e., pH, has exceeded a threshold value of 8, and the logger changes its call interval from its primary call interval of 30 minutes to its secondary call interval of 5 minutes, i.e. the logger now sends pH data to the communication server every 5 minutes. Later, an event 432 occurs, i.e., pH has fallen to 6 at time 434, i.e., 6:00 AM, when the logger reports to the server that the pH is now 6, which is below the threshold value of 8. At time 434 as a result of event 432, the logger switches its call interval back to its primary call interval of 30 minutes.

Figure 5:
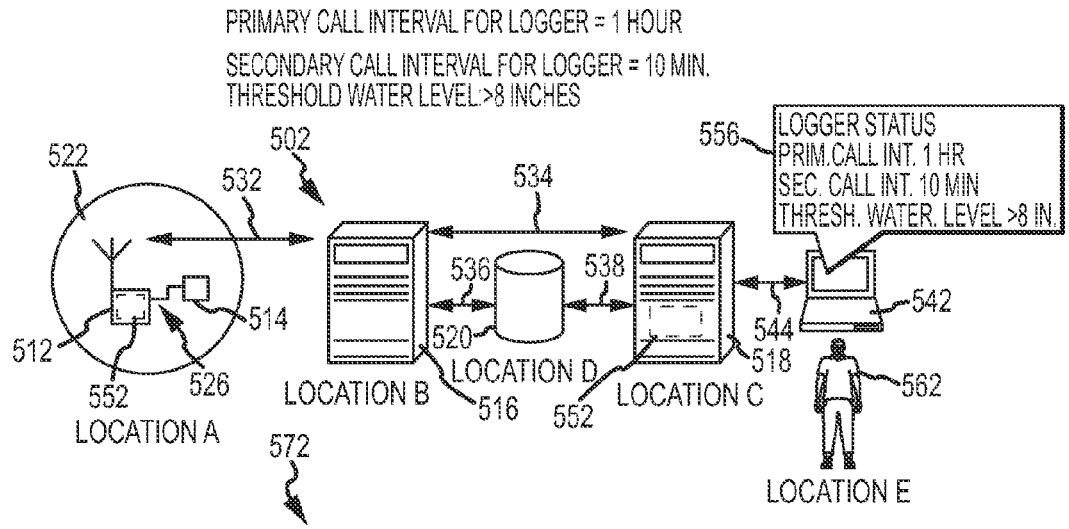
FIG. 5 is a diagram showing a logger changing its call interval based upon changes in environmental conditions according to one embodiment of the present invention.

FIG. 5 shows a water quality monitoring apparatus 502 according to one embodiment of the present invention that includes a logger 512 at a location A, a sensor 514 at location A, a communication server 516 at a location B, a web server 518 at a location C and a server database 520 at a location D. Logger 512 and sensor 514 are mounted on a manhole cover 522 of a wastewater collection system. Logger 512 and sensor 514 are in communication with each other via a communication link 526. Logger 512 is in wireless communication with communication server 516 as indicated by double-headed arrow 532. Communication server 516 is in bidirectional communication with web server 518 and server database 520 as indicated by double-headed arrows 534 and 536, respectively. Web server 518 is in bidirectional communication with server database 520 as indicated by double-headed arrow 538. Web server 518 is in wireless bidirectional communication with a visual display device 542 as indicated by double-headed arrow 544. Logger 512 and web server 518 each store part of a call interval modifying module 552 that is used to modify the call interval of the logger. The portion of call modifying module 552 that is stored and run on web server 518 is part of a web-enabled application displayed on visual display device 542 at a location E as part of a web browser 556 so that a user 562 can see information about the status of logger 512 and environmental data and so that the user can change the call interval of logger 512 based on the displayed environmental data.

FIG. 5 also shows a process for changing the call interval of logger 512. Logger 512 has a primary call interval of 1 hour, a secondary call interval of 10 minutes and a water level threshold of "greater than 8 inches," i.e., when the water level sensed by sensor 514 is greater than 8 inches, logger 512 switches to its secondary call interval of 10 minutes. At a time 572 (1 AM), sensor 514 senses a water level of 6 inches and logger 512 is calling in to communication server 516 at its primary call interval of every one (1) hour. At a time 574 two hours later (3 AM), sensor 514 detects the water level has increased to 10 inches. Because a water level of 10 inches is above the threshold level of 8 inches for logger 512, an alarm turns on in the part of call interval modifying module 552 stored on and run by logger 512 and logger 512 switches to its secondary interval of 10 minutes, i.e., the logger now sends water level data to communication server 516 every 10 minutes. Eighty (80) minutes later a time 576 (4:20 AM), sensor 514 detects that the water level has fallen to 7 inches. Because 7 inches is below the threshold level of 8 inches for logger 512, logger 512 switches back to its primary interval of every 1 hour. Logger 512 will then call in to communication server 516 forty (40) minutes later (5 AM) based on the primary call interval of 1 hour for the logger.

Although in FIG. 5, the primary call interval is based on a particular set of times that are 1 hour apart, the primary call interval (or secondary call interval) may also be based on when the last call was made to the communication server. For instance, in FIG. 5, the next call by the logger to the communication server could have occurred 1 hour later (5:20 AM) after the logger switched back to its primary interval.

A user may change the call interval of an environmental instrument directly by changing the call interval for the environmental instrument in a web-application or indirectly by changing a threshold level for the environmental instrument. For example, in FIG. 5 the user could change the threshold level for the logger to 11 inches, in which case the logger would not switch from its primary call interval to its secondary call interval unless the water level exceeds 11 inches.

Many forms of electrochemical sensors may be used in the systems of the present invention to detect the presence and concentration of ions in water. For example, the carbon nanotube sensors described in U.S. patent application Ser. No. 12/952,392 to Salzer et al., entitled, "Carbon Nanotube Sensor," filed Nov. 23, 2010 may be used in systems of the present invention and the entire contents and disclosure of this application are incorporated herein by reference.

Other sensors that may be employed in the systems of the present invention include the pH sensors described in U.S. Pat. No. 4,650,562 to Harman, and the entire contents and disclosures of this patent are incorporated herein by reference.

According to some embodiments of the present invention, examples of sensors that may be used with the remote water quality monitoring system may include any sensor known or used in the art. In addition to the variables listed above, the one or more sensors may be used to measure water level and/or flow velocity using any technology either known or later developed in the art. Such measurements may, for example, be used in combination to determine volumetric flow rate along with other known conditions and constants. For example, a sensor may also include a rain gauge. Examples of flow velocity or area flow velocity sensors that may be used with embodiments of the present invention may include wafer sensors and any sensor based on Doppler or ultrasonic, radar, pressure flow, electromagnetic (EM), magnetic (e.g., surcharge), etc., technology or detection. Examples of level, height or depth sensors that may be used with embodiments of the present invention may include any based on ultrasonic (look-down, submerged look-up, in-pipe, etc.), pressure (e.g., bubbler, surcharge, diaphragm displacement, etc.), radar, etc., technology or detection. According to some embodiments of the present invention, a height or level sensor may be combined with other structural elements or devices, such as flumes and weirs, to deduce other measurements or states, such as velocity in addition to water level, based on known relationships and constants. According to some embodiments of the present invention, any of the one or more sensors may further include an internal or external temperature sensor to provide, for example, auto correction for effects of temperature on any primary measurement by the sensor. According to some embodiments of the present invention, there may be a number of sensors at a particular location that obtain environmental data that may be jointly fed into an environmental instrument, such as a logger.

According to various embodiments of the present invention the one or more sensors detect or measure one or more of the following qualities of water in a water supply or water stream: temperature, chemical composition, total organic carbon (TOC), fluid quantity, flow rate, waste product, contaminant, conductivity, pH, dissolved oxygen, pressure, turbidity, permeate flow, chlorine or fluorine concentration, water or tank level, or equipment status or operation. The one or more sensors may be located at a plurality of locations within a particular geographic area.

According to some embodiments of the present invention, the one or more sensors may include any products on the market, sold, made by or branded under, for example, Hach™, Sigma™ or American Sigma™, Marsh-McBirney™, etc., either known or later developed in the art. Particular examples of the one or more sensors may include FLO-DAR®, FLO-TOTE®, FLO-MATE®, etc., sensors. For additional description of some types of sensors, see, e.g., U.S. Pat. Nos. 5,506,791, 5,633,809, 5,691,914, 6,208,943, 5,644,088, 5,811,688, 5,544,531, and 5,315,880, the entire contents and disclosures of which are incorporated herein by reference.

Electronic sensors may be used to detect or measure the amount of storage, discharge pressure and flow from a stream of water. Other parameters may be determined by analytical tests. Many of the sensors used to continuously monitor water streams are based on advanced separation processes employing selective ion membranes which concentrate the analyte for detection. For example, detection of chlorine may be mediated via an ion-selective membrane which may readily and specifically pass an analyte, such as free chlorine or hypochlorous acid (HOCl), thus separating and concentrating the analyte from the bulk solution. The sensors may incorporate multiple sensors as part of a single detector unit.

According to some embodiments of the present invention, the only communication link between the server and the environmental instruments and remote users of the remote water quality monitoring system is a wireless bidirectional communication link. Several benefits and advantages may be achieved by physically separating the storage, manipulation, analysis, reporting, etc., functions of the server and/or server database of the present invention from the site(s) or location(s) of data collection (i.e., sensors) within a remote water quality monitoring system.

According to some embodiments of the present invention, the server may be any type of computer, processor or device able to (1) at least temporarily collect, assemble, store, aggregate, etc., data from one or more sensors, and (2) transmit data or information to a server (or a server database associated with the server) via a mode of communication. Thus, a server may contain or include (1) a memory device(s) to collect, assemble, store, aggregate, etc., the data at least temporarily, (2) one or more ports or inputs for receiving data or information either directly or indirectly from one or more sensors, and (3) a transmission interface(s) to transmit data or information to a server. Such a server may further have the ability to process, manipulate, analyze, etc., the data obtained from the one or more sensors, such as by an analyzer or software located on the server, prior to transmission of data or information to the server and/or server database. The data sent from the server to the remote user/visual display device may be observational data synthesized from data derived from one or more environmental instruments.

According to some embodiments of the present invention, the logger may include one or more sensor ports for receiving data through cables, wires, etc., from one or more sensors. Alternatively, such a logger may be capable of receiving data wirelessly from one or more sensors. To store or log (at least temporarily) data or information received ultimately from the one or more sensors and/or manipulated or analyzed, the logger may include any type of memory device, such as a drive, flash or SIM card, etc. Thus, the logger may further include an analyzer or software to analyze or manipulate the data received from the one or more sensors. The logger may have a transmission interface, such as wireless connectivity or antenna or other connection outputs, for communicating via wireless transmission to a server.

According to some embodiments of the present invention, the analyzer may be one or more software program(s) on the server and/or the environmental instrument. Such an analyzer may perform analysis, calculation, comparison, manipulation, etc., of the data to generate an output, such as an analysis result, an analysis report, an alarm, etc., relevant to the monitoring of a stream of water, and the analysis, calculation, comparison, manipulation, etc., may be performed continuously, in real-time, at periodic or selected intervals, on condition or on demand. According to some embodiments of the present invention, an analyzer may be used to make calculations based on a combination of raw data from multiple sensors. When the analyzer is located on an environmental instrument, the analyzer may be used to generate or synthesize observational data derived from raw data obtained from a plurality of sensors. For example, independent data measurements of (1) flow rate and (2) water level by multiple sensors may be combined and used to calculate volumetric flow (in units of volume per time) based on the known dimensions and other constants regarding a water channel, pipe, etc., at a site within a water stream. Such multiple sensors used to measure volumetric flow may be connected to a common environmental instrument, such as a logger.

According to some embodiments of the present invention, the logger may have inputs, connectors or ports for one or more environmental instruments that may be automatically detected for plug-and-play options. The logger may be able to store or log data for a greater number of values or measurements than ports, such as up to 16 values. Each sensor port may receive data from a sensor comprised of multiple individual sensors. The logger may have different power options, such as battery power, auxiliary (external) battery power, reusable source (e.g., solar panel, etc.) and/or power from the electrical grid which may be combined with power switching (i.e., using battery or auxiliary power as a backup). The logger may have additional inputs, connectors or ports for receiving auxiliary power or a data communication link for connecting to a user computer or laptop. The logger may also have a user interface for providing basic indications/information, such as device or sensor status, connections, etc. The logger may be water-tight, enclosed, and/or have a rugged construction, may contain a desiccant to control moisture within the device, and/or may include a means for mounting the device. An example of a flow logger may include any FLO-LOGGER® product known in the art.

According to some embodiments of the present invention, the data may be transmitted to the server via an electronic control system connected with or coupled to the one or more sensors using any suitable wireless mode of communication. For example, a section of ladder logic or function block program code may be inserted into the code base of the electronic control system which directs the electronic control system to send specified data to the server and/or database. The communications protocol may be any protocol that is supported by the electronic control system which facilitates the transmission. For example, RSLinx®, a software program from Rockwell Software, may be operative on the server database computer to facilitate the transmission by a programmable logic controller (PLC). Alternatively, any number of commercial communications drivers may be used, such as those produced by commercial providers such as Kepware®, Wonderware®, and so on. In the case of an electronic control system typified by SCADA® or HMI® products, such as Wonderware®, RSView®, WinCC®, and other similar products, code blocks may be added to the control code to allow the operating program to collect and send data to the server. Thus, the steps of collecting data locally, possibly storing it temporarily, and subsequently transmitting this data to a server may be incorporated into the electronic control system.

According to some embodiments of the present invention, the data may be transmitted to a server via a computer that is part of an environmental instrument, such as a sampler either directly or through an electronic control system connected to or coupled with the one or more environmental instruments. According to these embodiments, the environmental instrument may transmit the data acquired or collected directly or indirectly from the one or more sensors to the server by any suitable mode of wireless transmission.

According to some embodiments of the present invention, after the data and information obtained from the one or more environmental instruments have been sent to the server of the water quality monitoring system, the server may analyze or manipulate the data to generate an output, such as manipulated data, an analysis result, an analysis report, an alarm, etc. Alternatively, the environmental instrument may analyze or manipulate the data obtained from the one or more sensors and the data may then be transmitted to the server and the server may then further analyze or manipulate the data and information to generate an output. However, the output may be generated, presented, uploaded, etc., by the server without further analysis or manipulation by the server. The analysis, manipulation, etc., of the data may be performed by an analyzer, such as a software program or routine, firmware and/or hardware, that may be housed on the environmental instrument, the server and/or the server database associated with the server.

According to some embodiments of the present invention, the one or more sensors may be optionally integrated into or connected to an electronic control system. Examples of an electronic control system may include an in-house supervisory control and data acquisition system (SCADA) or a programmable logic controller (PLC). The electronic control system may be composed of any available commercial devices for converting analog to digital, such as analog-to-digital boards, specifically designed for the purpose of converting instrument readings or data to computer-readable form. Thus, the remote water quality monitoring system of the present invention may utilize existing instrumentation and control systems as well as existing communication devices. The electronic control system may perform basic analysis of the raw data to produce an analysis parameter that may then be sent to the server. According to some embodiments of the present invention, the electronic control system may continuously scan the sensor data and automatically log and archive the data at specified intervals. According to some embodiments of the present invention, raw data obtained from a sensor may be stamped or labeled with time and location information, such as a unique identifier(s), for aiding subsequent analysis or manipulation. Raw data obtained from a sensor may also be labeled according to the particular order in which the data are sent to a server. According to some embodiments of the present invention, the electronic control system may include a transmission interface which functions to transmit the data to the server.

According to some embodiments of the present invention, a local configuration file on the environmental instrument may "tell" a program in the environmental instrument which of the register addresses of the electronic control system to access, any scaling factor that needs to be applied, a physical description of the data being collected, etc. The data set collected may then be converted into a form for transmission, such as a comma delimited string value, and perhaps stored locally and possibly encrypted for security on a storage medium such as a hard disk, etc.

According to some embodiments of the present invention, the data and information obtained by an environmental sensor may be manipulated by a processor in the environmental sensor to generate an output, such as an analysis result, report, alarm, etc., that may be communicated to a user/visual display device via a server. Such data or information transmitted from an environmental instrument may include observational data which is calculated, manipulated, etc., by an analyzer on the environmental instrument from data derived from one or more environmental instruments. According to some embodiments of the present invention, the data and information may be analyzed, manipulated, etc., by analyzer(s) located on remote environmental instruments.

According to some embodiments of the present invention, a server database or software-implemented server database may be associated with the one or more servers for storage of data. The server database may be on the server or exist as a separate unit, and the number of server(s) and/or database(s) may be varied to suit a particular application, network traffic or demands of a particular client. According to some embodiments of the present invention, for example, the one or more servers may comprise a computer, an FTP server, a server database, and/or a web or Internet server, which may each be located at the same or different locations and use any available and appropriate operating systems. This storage on the server database may take many forms such as flat files, spreadsheets, and relational or non-relational databases. According to some embodiments of the present invention, the server database may be a relational database, such as Microsoft SQL Server or Oracle database products.

According to some embodiments of the present invention, the data may be wirelessly transmitted between the environmental instruments, the server(s) and/or the user/visual display device continuously, in real-time, at periodic or selected intervals, on condition, or on demand by a user. The data also may be encrypted for additional security and may be decoded by the server and/or the server database and placed in the appropriate locations.

According to some embodiments of the present invention, the data may be transmitted to the server by environmental instruments comprising the one or more sensors. According to these embodiments, the one or more environmental instruments may be fitted with communications processors which enable the sensors to send data directly to the server. Suitable environmental instruments may include sensor assemblies having a transmission interface effective for real-time data transmission, such as a LonWorks® network variable interface. Suitable sensors may also include, for example, the Six-CENSE™ and the CT-CENSE™ manufactured by Dascore, Inc., as well as the multi-sensor devices manufactured by Sensicore, Inc. In this example, sensors may transmit the data to a server by any suitable wireless mode of communication, such as a cell network.

According to some embodiments of the present invention, data may be displayed or presented as an output, such as an analysis result(s) and/or analysis report(s), in a predetermined format, which may then be sent to a user, such as, for example, a consumer, public official, authorized personnel or regulatory agency. Indeed, the data may be manipulated and formatted into an output or analysis report as required for submission to a regulatory agency. According to some embodiments of the present invention, the analysis or manipulation of data may be presented as an output that is uploaded onto a web server and made accessible via a web browser for presentation to, for example, a public official, consumer or interested member of the public. Alternatively, according to some embodiments of the present invention, an output in the form of an alarm may be sent to alert a user of a problem or deviation from normal conditions.

According to some embodiments of the present invention, one or more output(s) may be sent, presented or uploaded to one or more remote viewing device(s) in one or more formats having different levels of sophistication or complexity based on their intended recipient(s) or user(s), even if such one or more output(s) relate to the same data or information. According to some embodiments of the present invention, an output, such as an analysis result or analysis report about current data, may be presented alongside and/or in comparison to historical records. An output may also be used to present scheduled and predicted maintenance reports. For example, the output may provide or present preconfigured performance information, maintenance, quality assurance, quality control, regulatory, cost reports, performance evaluation, graphing, historical trends, regulatory reports, plant or facility process, operating and economic information, indications and scheduling for preventive maintenance, troubleshooting, etc. According to some embodiments of the present invention, access to an output of the present remote water quality monitoring system may depend on the security measures in place, such as a login and password or other identifying criteria.

However, according to some embodiments of the present invention, a simplified presentation of the data in an output of the remote water quality monitoring system may be beneficial to even a trained remote user. Accordingly, a graphical and/or color-coded presentation of the data or analysis or manipulation of the data may potentially be used in any output format or report. A graphical presentation may include any suitable graphical format, such as tables, pie charts, bar graphs, etc., that may aid in the presentation of the output or report. Color coding may be used, for example, to provide an indication of normal or abnormal operation, as well as warning status or alarm conditions. An output of the remote water quality monitoring system may also show data or analysis or manipulation of the data in a geographical layout or form to help track or pinpoint the origin or cause of a problem. Historical data or expected values may also be shown with current data for comparison. When an output is provided to a trained remote user, the data and/or analysis may be presented as an exception report showing all instances in which data triggered an alarm or was close to a trigger point.

According to some embodiments of the present invention, when an output is sent or presented to management, the outputs or reports may be generated for three primary management levels: (A) process systems operations, (B) plant quality assurance (QA)/quality control (QC), and (C) financial oversight. For instance, an output or report for operations of a process system may contain information necessary to monitor, maintain, supervise and troubleshoot process plant system performance. In this manner, typical information and parameters may include, if applicable, flow rates, pressures, delta pressures, permeate and/or ion exchange quality, pH, alarm conditions, tank levels and a graphical presentation of applicable process performance parameters and trends.

According to some embodiments of the present invention, an output including data, analysis results, analysis reports, etc., may be sent to a remote viewing device using any appropriate or suitable wireless mode of communication. The output may be in any suitable file format, such as but not limited to html, jpeg, gif, pdf, etc., based on the output type and/or remote viewing device. The output may be sent in a suitable and/or tailored format to preselected recipients, such as authorized personnel, law enforcement and/or regulatory agencies, in the event of an emergency or abnormal condition or operation. The content of the output may be kept confidential, and access to the output, including data, analysis results, analysis reports, etc., may be controlled by encryption or the use of appropriate account names, protocols and passwords. Multiple parties or persons may be notified of, have access to or receive outputs from the remote water quality monitoring system, thus allowing redundancy in sending notifications, alarms, analysis results, analysis reports, etc.

According to some embodiments of the present invention, the wireless mode of communication for sending an output to, or allowing access to an output by, a remote viewing device may vary and may use any suitable technology. For example, according to some embodiments of the present invention, an output including data, analysis results, analysis reports, etc., may be uploaded to an Internet or a web server for access, visualization or downloading by a remote viewing device, such as by using a web browser. According to some embodiments of the present invention, the Internet server or web server may be the server of the remote water quality monitoring system or may be a separate computer or server. According to some embodiments of the present invention, the output may be uploaded to an Internet server or a web server for access with little or no manipulation or analysis by the server, visualization, or downloading by a remote viewing device by a user. According to these embodiments, for example, the data or information derived from the one or more sensors may first be analyzed or manipulated by the environmental instrument prior to being transmitted to the server. By making the output available on an Internet server or a web server, the communication or dispersion of the output, including data, analysis results, analysis reports, alerts, alarms, etc., may be greatly facilitated and may involve any interested or authorized recipients. For example, any authorized recipients may access data, analysis results, analysis reports, alerts, alarms, etc., of the output on a webpage by accessing the data, information, output, etc., asynchronously from the Internet server computer. Furthermore, the output, including data, analysis results, analysis reports, alerts, alarms, etc., may be continuously or regularly updated and made available in near-real-time.

According to some embodiments of the present invention, the wireless mode of communication for sending an output to, or allowing access to an output by, a remote viewing device may include other suitable technologies, such as, for example, by facsimile, file transfer protocol (FTP), voice or text messaging, text-to-voice telephone messages, electronic mail, pager, human voice calling, SMS messages, instant messaging or groupware protocols, the Internet, a cellular network, wireless or satellite communication, radio communication, etc. Examples of visual display devices that may be used by a remote user with various embodiments of the present invention may include, for example, personal computers, servers, etc., as well as a variety of personal communications equipment, such as PDAs, cell phones, pagers, BlackBerrys®, Palm® devices, iPhones®, etc. According to some embodiments of the present invention, the remote viewing device may be the same as the server of the present remote water quality monitoring system.

Another advantage of some embodiments of the present invention, for example, is the ability to send an output or other data, information, etc., about a water stream to a remote viewing device via a wireless mode of communication, which may reduce the need for operators or authorized personnel to visit the site of the water stream being monitored, maintained, etc. This may reduce the costs associated with monitoring a water stream if data had to be collected locally or by direct connection to a device or environmental instrument. This is especially true if the remote water quality monitoring system is further combined with sensors and other devices that require less maintenance and service, such as sensors that do not contact the water and are able to operate reliably for longer periods of time without maintenance or service.

According to various embodiments of the present invention, the wireless mode of communication between the environmental instruments and the server, between the environmental instruments at different locations, between the server and visual display devices at remote locations, etc., may vary and may be accomplished via one or more of the following: the Internet, TCP/IP, Ethernet, file transfer protocol (FTP), e-mail, SMTP, cellular phone networks, radios or remote terminal units (RTU) coupled to radio frequency transmitters, satellite transmission, a wireless network, a wide area network (WAN), a wireless local area network (WLAN), etc. According to some embodiments of the present invention, the data may be transmitted from the environmental instruments to the server continuously, in real-time, at periodic or selected intervals, on condition or on demand by a user.

Some of the embodiments of the present invention may be used to monitor a water treatment system. Such a water treatment system may comprise a water treatment core facility that is a water treatment facility for the distribution of potable drinking water to the public, and the water treatment system also may comprise a distribution system. According to some embodiments of the present invention, the water treatment system may comprise a water treatment core facility that is a WWTP, and the water treatment system may further comprise a collection system.

Municipal drinking water may be obtained from a variety of sources that can be made potable by use of proper water treatment equipment. For example, a reverse osmosis system may be used to lower the total dissolved solids from sea water with minimal pretreatment to produce potable drinking water. Despite the sophistication of pretreatment of seawater, improper monitoring or operation can allow the seawater to quickly foul membranes. If fouling occurs, but is found quickly, the membranes may be cleaned, and complex and costly water contamination and associated water treatment repairs may be averted. However, if the fouling is not detected quickly through proper monitoring, the membranes can be irreparably damaged, and expensive partial or total membrane replacement would be required. The cost of unplanned membrane replacement, not including the lost revenues typically associated with downtime, can make such a system cost prohibitive.

Increasingly, the need for pure water is causing more and more municipalities to install wastewater recovery processes to recycle municipal WWTP effluents back into water of suitable quality to be used for potable drinking water or irrigation. For example, such recovery processes may recover secondary treated municipal effluents using reverse osmosis, and then inject the recovered effluents back into an aquifer. More and more of these installations are being planned throughout the United States and the rest of the world.

One difficult aspect of treating municipal wastewater effluent is that neither the flow rates nor the mix of contaminants is constant. This is particularly true for a municipal WWTP with collection systems that include a variety of industrial discharge sources in addition to the usual sanitary discharges from homes, businesses, schools, and so on. While the sanitary discharges are well characterized in terms of composition and treatability, the addition of industrial wastes means that the WWTP must plan for a wide variety of contaminants. In general, most WWTP systems cannot deal effectively with every situation. Even with excellent design and engineering, the large fluctuation in the type and quantity of contaminants reaching the WWTP often results in varying levels of effective treatment of the discharge from the WWTP. For a tertiary water recovery plant treating the effluent from the WWTP, this can be particularly difficult, because many contaminants are not readily removed even by processes such as reverse osmosis. In addition, certain contaminants can also foul reverse osmosis, ultrafiltration and microfiltration membranes, causing loss of performance or membrane damage. Therefore, it is important that wastewater treatment plants be monitored to ensure that contaminants are properly removed before discharge or reuse of effluents back into the environment to thereby avoid damage to expensive equipment.

Another application in which water quality is important is with wastewater treatment plants. The treatment and subsequent recycling of wastewater is a cornerstone of the quality of life in the industrialized world. Cities, industries and agricultural operations produce large quantities of wastewater, all of which must be treated to some degree to remove contaminants or pollutants before the water is suitable for recycling or discharge into the environment, such as streams, rivers or oceans. In metropolitan areas, central waste water treatment plants must treat water from a variety of sources including city, industrial and agricultural wastewater. In many cases, generators of industrial wastewater are required to install and operate wastewater treatment plants at their own sites before discharge into central water collection systems. At the central water collection system, industrial wastes generally may be mixed with domestic or city wastewater and other untreated waste sources. These mixed wastes are then transported to the central wastewater plant or sewage treatment facility for final treatment before discharge.

Some embodiments of the present invention also provide a system and method for remotely monitoring, storing, analyzing, manipulating, uploading, reporting, etc., information and data relating to water quality and/or treatment derived from raw data obtained from a plurality of sensors of a water treatment system, which may be strategically placed to gather data or information necessary for analysis or manipulation. Such information and data may be remotely stored, manipulated, etc., on one or more servers, and/or stored on one or more removed databases, which may be associated with the one or more servers. A water treatment system, according to some embodiments of the present invention, may include any system designed or used to generate water or a water-based product having a predetermined, desired or preferred set of characteristics, qualities, properties, etc., for a particular application, such as, for example, a municipal potable drinking water treatment facility, a system generating water for a manufacturing process, etc., as well as any distribution system. A water treatment system may also include any system designed or used to process or treat a water-based substance into a product discharged into the environment, such as, for example, a central WWTP, etc., as well as any collection system. Water treatment systems may include public or municipal systems as well as systems dedicated to a real estate development. For example, a water treatment system may include any system, plant or facility that uses equipment based on advanced separation, filtration, dialysis, ion exchange processes or any other basis, technology or mechanism for processing, treating, detecting, purifying, isolating, separating, etc., water according to relevant parameters.

According to some embodiments of the present invention, the one or more sensors may be used to obtain relevant raw data about the operation of a water treatment system and/or the quality of water being processed, treated, received, distributed, etc., that would be relevant to the analysis, manipulation and evaluation of the data in generating an output, such as an analysis result, analysis report, alarm, etc. For example, each of the one or more sensors may be used to measure, quantify or detect the following characteristics, conditions, qualities, properties, etc., of water. Examples of characteristics, conditions, qualities, properties, etc., of water that may be measured by the one or more sensors may include, but are not limited to: temperature, chemical composition including total organic carbon (TOC), total suspended particles, quantity, flow rate, and types and amounts of waste(s) such as those commonly discharged into streams from wastewater treatment or industrial sites. Further examples of characteristics, conditions, qualities, properties, etc., of water that may be measured by the one or more sensors may include one or more contaminants, conductivity, pH, pressure, turbidity, permeate flow, dissolved oxygen, chlorine or fluorine concentrations, tank or water levels, and equipment status and operation. According to some embodiments of the present invention, the one or more sensors may be chosen to generate data or information for a regulatory report necessary to enable a regulatory agency to determine operational parameters and quality and quantity of the treated water such as water production rate (flow), treated water consumption rate (flow), treated water storage volume, reserve capacity (at current production and consumption rates), final treated water quality, reports and archive data for regulatory compliance and/or QA/QC documentation.

According to some embodiments of the present invention, raw data about the operation of a water treatment system or the characteristics, conditions, qualities, properties, etc., of water processed or treated by a water treatment system may be acquired, collected, detected, measured, etc., by one or more sensors or probes placed at one or more sites or locations within or throughout the water treatment system, such as a plurality of locations within or throughout the water treatment system, that may include locations in the field, i.e., in a collection or distribution system. Sensors may be strategically placed to gather relevant data and information at appropriate sites or locations and/or provide logical functional groupings for review and analysis.

According to some embodiments of the present invention, once the data is analyzed or manipulated into an output, such as an analysis result or analysis report, the output may be sent by any known, available and/or suitable wireless mode of communication from the server to a remote viewing device for viewing by a user. According to some embodiments of the present invention, the output may be sent to the remote viewing device or accessed by the remote viewing device continuously, in real-time, at periodic or selected intervals, on condition or on demand. For example, the output may be a notification, alarm or alert, such as an Alarm Event, sent on condition of an emergency or abnormal, harmful or dangerous quality, state or condition relating to a water stream. Such an output may include a notification of failures, shutdowns, exceeding of critical parameters, equipment damage, etc. Alternatively, for example, the output may be composed as an analysis report, which may be in a format for submission to a regulatory and/or law enforcement agency. The remote water quality monitoring system may send, present or upload an output as a weekly, monthly, yearly, etc., summary of performance, water quality or other information that may be reviewed by management for the water treatment system or by elected officials, customers, vendors or members of the public. Alternatively, the remote water quality monitoring system may send, present or upload an output continuously, on condition or on demand of a user. When sent or presented, the output may reflect or show updated information and recently collected data.

According to some embodiments of the present invention, the format and sophistication of the presentation of the output will likely depend on the intended recipient(s) or user(s). For example, an output, which may include any relevant information, data, analysis results, analysis reports, etc., about the operation of a water treatment system or the quality, properties, etc., of water processed or treated by the water treatment system, may be presented in a more sophisticated form when presented to internal management or operators of the water treatment system than when presented to elected officials, customers or members of the public.

According to some embodiments of the present invention, the output may be used to report or present information or analysis of the operation or conditions in a WWTP, particularly as the output relates to health and safety concerns. The analysis result may take many different forms; however, one form may be a prediction of the water composition and flow rate in terms of selected parameters of interest that may arrive at a WWTP as a function of time. Thus, for example, the server may be operable to calculate a predicted concentration of various components at the time of their arrival at a central WWTP and compare the computed values with pre-established and/or historical parameters.

According to some embodiments of the present invention, the output may be a report submitted to a regulatory agency in a required format, such as visual graphs, statistical reports or a compliance calendar, to meet the reporting requirements of the agency, and such reporting or sending of the output may be performed automatically. Quality and safety standards for potable water are regulated by the Environmental Protection Agency (EPA) in accordance with the Public Water System Supervision program. The standards are enforced by local agencies. There are over 170,000 water districts in the United States that provide public drinking water to 90% of Americans. The EPA issues primary standards designed to protect public health against substances that may be harmful to humans if consumed. EPA secondary standards ensure that aesthetic qualities of water, such as taste, odor or clarity, are met. However, each water district remains responsible for monitoring the drinking water itself to ensure that it meets all drinking water standards. The treatment processes for drinking water must be monitored as well. Therefore, the remote water quality monitoring system of the present invention may be useful not only in monitoring whether these standards are met on a routine and continuous basis, but also in providing automatic generation of regulatory reports as an output to an agency in the required format.

According to some embodiments of the present invention, the output of the remote water quality monitoring system may be a regulatory report sent to the Department of Homeland Security and/or law enforcement agencies in situations appearing to suggest deliberate tampering with a water treatment system, such as by an act of terrorism. Embodiments of the present invention may be able to carry out sophisticated calculations, manipulations, analyses, etc., to detect tampering events and perhaps distinguish those events from normal malfunction or mismanagement.

According to some embodiments of the present invention, the output may be in any format and may incorporate a tabular or graphical display as may be suitable to facilitate or focus the presentation of the data or analysis or manipulation of the data for a particular user. According to some embodiments of the present invention, the output of the remote water quality monitoring system may be a simplified presentation for a non-technical user who is untrained or lacks detailed knowledge about the operation of a water treatment system, such as a customer, elected official or member of the public. For example, municipal water treatment plants are ultimately the responsibility of elected officials. Yet these officials rarely have the technical training or time to allow them to directly access the performance parameters of the systems for which they are responsible. Embodiments of the present invention may easily be used to provide a readily understandable presentation output of the current performance of a municipal water treatment system. Such an output may be made accessible to the public, such as via the Internet by uploading onto a web page, thus allowing interested members of the public to monitor the operation of their own drinking water plants, as desired. In providing a simplified presentation of the data to the non-technical user, operating parameters may be color-coded and displayed graphically or in a tabular format, etc.

The presence or absence of turbidity in the water supply may greatly affect the amount of disinfectant required to achieve inactivation of biological organisms. The suspended particles producing turbidity are usually removed in the water treatment process before disinfection agents are applied. However, turbidity breakthroughs do occur, and failure to quickly raise the disinfection dose level may lead to insufficient disinfection residuals reaching the distribution system. This may present a threat to public health, particularly if the drinking water supply is contaminated either deliberately or inadvertently.

For example, in the context of a water treatment facility for providing potable drinking water to the public, data regarding disinfectant concentration and turbidity from both the treatment facility and the distribution system may be analyzed, and historical information as well as known constants may be used to predict expected conditions at points downstream within the distribution system based on expected lag times and the effluent conditions from the treatment facility. For example, data may be collected from the water treatment facility about relevant information, such as chemical dosing rates, filtered water turbidity, chlorine residual, etc., as well as data from sensors in the distribution system, such as chlorine residual, etc., may be used for comparison. With historical data as a reference point, one can calculate a chlorine demand from the chemical dose rates, flows and residual using the current data. Chlorine demand may be defined as the actual amount of chlorine that is reacting, typically calculated as free chlorine dosed less the residual chlorine. Chlorine demand may be correlated with temperature, season and filtered water turbidity. Additionally, residual chlorine leaving the plant may be correlated with residual chlorine within the distribution system. If the actual chlorine residual measured at the distribution system point of measurement varies from the historical values expected from the chlorine residual leaving the treatment facility by more than a set percentage or number of standard deviations, then an alarm or alert may be issued by the remote water quality monitoring system according to some embodiments of the present invention.

As another example in the context of a water treatment facility providing potable drinking water to the public, data obtained from the one or more sensors may be combined with known system constants such as flow rates, residence times and so on to continuously generate a calculated product of disinfectant concentration times contact time $C*T$. This simple factor alone is quite useful in predicting the amount of biological organism deactivation.

As another example in the context of a WWTP, an analysis or manipulation of data obtained from sensors at upstream locations in a collection system, such as sites or locations of discharge from water treatment or industrial wastewater plants, to detect the amount of contaminants or pollutants, may be used to predict the future composition and flow rate of water arriving at the central WWTP. This may be accomplished in a simple manner by using known or expected constants and information as well as historical records about transit time, flow rates and patterns, etc., from each of the relevant sites or locations upstream, such as within the collection system and at or near points of discharge. Any results, conclusions, reports, etc., generated using such an analysis or manipulation may be used to alert operators of a central WWTP receiving wastewater from the collection system of a potential overload so that appropriate precautions and changes in operation may be made. As will be readily appreciated by those skilled in the art of data analysis, this can provide a powerful indicator of either normal conditions expected at the WWTP or out-of-bounds conditions that may require immediate action and notification of responsible parties.

According to other embodiments of the present invention, the projected or remaining life of equipment, such as a membrane, may be determined or estimated by the remote water quality monitoring system based on operational performance data. Efficiency levels for equipment or a water treatment system as a whole may be determined by the remote water quality monitoring system relative to a theoretical potential or efficiency, which may be based on a theoretical minimum water, power and chemical consumption versus actual consumption calculated. In addition, financial and economic reports may be generated based on performance and/or consumption data. Furthermore, the data may be analyzed and compared to federal and/or state regulatory requirements for water quality and environmental protections.

A plant QA/QC output or report, for example, may contain information necessary to enable plant managers to effectively manage downstream manufacturing or distribution processes. In addition, quality assurance personnel may be able to monitor the quality and quantity of the treated water to confirm compliance with specifications and standards. Information in this report may typically include treated water production rate (flow), treated water consumption rate (flow), treated water storage volume, reserve capacity (at current production and consumption rates), final treated water quality, reports and archive data for regulatory compliance and/or QA/QC (quality analysis/quality control) documentation.

Financial oversight may be achieved with a plant economic output or report that may contain information needed by managers with profit-and-loss or budget responsibility to effectively track the cost of operation and to identify budget variances when they occur, to permit timely corrective action. For this purpose, the data parameters contained in a plant economic report may include calculated power consumption (expressed in kWh and actual cost in local currency) that is computed on the basis of user's supply pump/motor efficiencies both as a year-to-date measurement and as a percentage of the prior period and variances both actual and budget/actual versus prior period. The parameters may also include calculated chemical consumption (expressed in volume consumption and as converted to local currency) and computed based on the user's supplied chemical dose rates and integrated feed water flow rates. This may be shown in the output or report as a year-to-date measurement, as a percentage of the prior period, or as variances of both actual and budget/actual versus prior period.

According to some embodiments of the present invention, an analyzer on the environmental instrument, the server and/or server database associated with the server may also interpret and consider any identifier(s) or configuration files associated with the data that may indicate or identify the origin, location and time of the data capture from the one or more sensors. The analysis and calculation of the data may further be performed by the analyzer to determine or indicate performance, evaluation, preventive maintenance, scheduling, optimization and troubleshooting of the operation of the water treatment system or equipment, in addition to monitoring water quality. For example, the data may be compared to known or expected performance data or parameters to calculate a differential, which may be used to determine whether the water treatment system is performing within a normal range or out of bounds if a predetermined differential is exceeded. Such comparisons may be based on the amount or concentration of, for example, a disinfectant, contaminant or pollutant present at different locations in a water treatment system. If the differential is exceeded, then appropriate persons, operators and/or agencies may be alerted. Alternatively, for example, the data may be compared to known, expected or historical data or values to determine if the operation of the water treatment system is optimized.

According to some embodiments of the present invention, the analyzer may convert the data into a consistent set of units, and thus translate all values into a common format, such as pounds per square inch (psi) for pressure, etc., using a unit's conversion sub-program to allow for appropriate comparisons and calculations. Furthermore, the data may be normalized to specific configurations and conditions for a water treatment system. For example, the feed pressure may be critical in determining the future and current performance of a system in reference to its performance when new. For reverse osmosis membranes, changes in pressure are related to age, production rate and temperature and vice versa. Thus, a change in flow rate may or may not indicate that the overall system's performance has changed when normalized and compared to its performance when new or recently cleaned. Prior to this invention, the complex mathematics for these conversions required some manual intervention on the part of the operator to compute the normalized conditions. Embodiments of the instant invention may do this automatically and report normalized data to the output.

According to some embodiments of the present invention, the analyzer or software of the present remote water quality monitoring system may be used to make any suitable statistical inferences, derivations, conclusions or predictions from the data, especially based on a comparison to historical data or expected values. Such an analysis or manipulation of the data may provide an indicator of either normal or abnormal operation of a water treatment system or characteristics, properties, qualities, etc., of water processed or treated by a water treatment system. According to some embodiments of the present invention, the analyzer may be used to predict conditions, such as the presence, quantity or concentration of a disinfectant, contaminant, or pollutant at a downstream location at a later point in time based on data obtained from sensors at upstream locations within a water treatment system.

According to some embodiments of the present invention, the data acquired or collected from the one or more sensors may be compared by the analyzer to expected or historical performance data or records and/or to any known values and constants, such as known or expected transit times, location-specific flow rates and patterns and distances within different portions of a water treatment system, known physical and chemical properties and characteristics of water, contaminants, disinfectants, pollutants, etc., using any known equations, algorithms, etc., which may be used to model, predict or compare the performance of the water treatment system or the quality of water processed or treated by the water treatment system. Data acquired or collected from the one or more sensors may be compared to each other and/or to historical data, and calculations may be performed to generate an output, such as one or more analysis results, etc. According to some embodiments of the present invention, the analyzer or software may perform any calculation, computation, comparison, analysis, etc., that would be relevant, suitable or appropriate to monitoring the operation of a water treatment system or the processing or treatment of water in a water treatment system.

One advantage of some embodiments of the present invention is that remote storage and manipulation of water quality and treatment data may make the operation of a water treatment system safer and less susceptible to tampering or control by unauthorized individuals or outsiders by separating the operation and control of the water treatment system from the data analysis, manipulation and/or communicating or reporting functions of the present invention. For example, this feature may be useful in detecting direct tampering, such as an act of terrorism, by an individual or outsider, with a water treatment system. According to some embodiments of the present invention, since the server of the remote water quality monitoring system is physically separated from the operation of the water treatment system, it is unlikely that an individual tampering with a water treatment system would also have access to the remote water quality monitoring system, especially since access to the remote water quality monitoring system may be controlled or password protected. According to some embodiments of the present invention, if a hacker were to remotely access the remote water quality monitoring system of the present invention, the hacker would not be able to directly access and control the operation of the water treatment system because the server and database are external, physically remote and not connected to the process facility being monitored, except perhaps via a wireless mode of communication.

Yet another advantage of some embodiments of the present invention is that data and information may be combined, pooled, compiled, etc., from sensors placed at multiple locations or sites throughout a water treatment system and in the field as part of a broader distribution or collection system. According to some embodiments of the present invention, sites or locations within the distribution or collection system may be considered part of the water treatment system, even though the distribution or collection system may operate independently of a water treatment core facility of the water treatment system. Such sensors located at the multiple locations or sites may operate independently and/or have no communication between sensors other than the remote water quality monitoring system of the present invention. By comparing data from these multiple independent sites or locations, a more advanced form of analysis and conclusions may be performed or made in view of the water treatment and distribution systems as a whole. For example, better prediction and anticipation of downstream contamination events may be made by having multiple data points obtained from sites or locations throughout a collection or distribution system associated with the water treatment system, thus allowing appropriate actions to be taken downstream to lessen or prevent the impact or damage caused by the contamination event, such as the introduction of dangerous, poisonous or unhealthful contaminants into the environment or drinking water.

For example, the water treatment core facility may be a central WWTP that receives waste released from multiple sources upstream that converge into a common collection system that feeds into the central WWTP. The collection system may serve numerous wastewater treatment sites or industrial waste sites that feed into a central WWTP. According to some embodiments of the present invention, multiple sensors may be placed throughout a collection system, including the water treatment and industrial waste sites, to monitor discharge into the common collection system. Water treatment sites may include cities, manufacturers, agricultural operations, etc., which treat wastewater before it is discharged into the common collection system. For a WWTP operator, an accurate prediction of the composition of incoming wastewater would be highly beneficial for the efficient operation of the WWTP facility.

According to some embodiments of the present invention, the composition of influx water in a WWTP serving a geographically distributed wastewater collection system may be estimated from measurements taken from sensors located upstream, such as at or near wastewater treatment sites or industrial waste sites discharging into the common collection system. Since the water flow patterns, water transit times and the composition of water leaving each of the treatment or industrial sites within the wastewater collection system may be known, the expected composition of influx water arriving at the WWTP can be calculated and reliably and quickly transmitted to the operators of the central WWTP and/or remotely to other entities or persons, such as through a remote viewing device. In addition to known information, the volumetric flow rate may be measured using the one or more sensors. This advance notice allows the WWTP to respond to varying contaminant or pollutant introductions in a far more effective manner than at present, where the first knowledge or information may come after the contaminants have already entered or even passed through the system. For WWTP entities that operate reclamation facilities downstream of the WWTP, this advance knowledge is even more valuable, because it allows the reclamation facility to modify its operations as necessary to prevent damage to the process facilities. It will be readily appreciated by WWTP operators that knowledge of the incoming wastewater composition would be of great benefit in assuring the continued operation of the central facility at top efficiency.

One advantage of some embodiments of the present invention is that the remote water quality monitoring system of the present invention may create a layer of redundancy that may be independent of and/or complementary to the direct monitoring carried out by qualified individuals at a water treatment system or facility to safeguard operation of the water treatment system. Redundancy may also be achieved by, perhaps simultaneously, reporting analyzed or manipulated data to multiple persons and/or entities in the same or different format. In addition, the remote water quality monitoring system may reduce or eliminate the need for direct human involvement. By having the remote water quality monitoring system automatically perform the calculations and manipulations on the raw data in real-time without direct human involvement, there may be less human error in evaluating, analyzing, etc., water quality and the operation of the water treatment system.

Another possible advantage of some embodiments of the present invention is that the data may be transmitted to a server where more advanced computations, manipulations, analysis, etc., may be performed prior to reporting, uploading, etc., an output, such as an analysis result, analysis report or alarm, to a user. A software program on the server may be more sophisticated than may be achieved locally, such as with the local electronic control systems used to control and operate the water treatment system, plant or facility. This may allow for the processing power of existing control systems to not be impaired or impacted. For example, an analysis report generated by manipulation of the data on a server may include a submission to a regulatory agency to meet reporting requirements in the format required by the agency, and such reporting may be performed automatically. The remote analysis, manipulation, etc., may be performed quickly and automatically to remotely monitor operation and water conditions in real-time, continuously, at selected, periodic or regular intervals, on condition or upon demand of a user and rapidly generate multiple types of outputs, such as alarms, analysis results, analysis reports, etc., to one or more users. For example, the software program may separately generate a detailed regulatory report for submission to a regulatory agency, send a simple alarm to authorized personnel to alert of a contamination or equipment failure, and/or post data and information about the water treatment system on a web page for access by members of the public. Alternatively, the analysis, manipulation, etc., of data and information may be performed locally on the environmental instrument, such as a logger. According to some embodiments of the present invention, such analysis, manipulation, etc., of data and information on the environmental instrument may be performed in addition to further analysis, manipulation, etc., of data on the server.

Yet another advantage of some embodiments of the present invention is that greater flexibility and accessibility may be achieved over existing systems by allowing a user access to the server to receive data, information, reports, etc., sent by any known means or wireless mode of communication from the server. By having greater accessibility and communication of data, information, reports, etc., greater coordination may be achieved between different parts of the water treatment system and any associated collection or distribution system, which may include, for example, remote sites or locations of industrial waste discharge in the case of a WWTP.

Yet another advantage of some embodiments of the present invention is that the remote water quality monitoring system may be implemented with moderate cost, because the remote water quality monitoring system may be incorporated or interfaced with existing sensors and/or an electronic control system of a water treatment system without modification of the design or layout of the water treatment system. Furthermore, the data collected from the water treatment system may be transmitted electronically to the server using, for example, existing communication networks.

Another advantage of some embodiments of the present invention is that the cause, scope or location of a problem or source of contamination may be better determined, tracked or distinguished by having more independent data points of reference obtained from sensors at sites or locations throughout a water treatment system, such as sites or locations in a water treatment core facility as well as throughout a collection or distribution system, i.e., in the field. Such analysis or determinations may be aided by the existence of historical data and known information about the operation of the water treatment system in relation to its environment which may be used for comparison. For example, a chemically or biologically active agent may be deliberately injected into the distribution system at a point downstream of a potable drinking water treatment facility. A sophisticated terrorist might first inject a chlorine scavenger, such as sodium metabisulfite, into the distribution system to eliminate the residual chlorine normally present. At some point downstream of the metabisulfite injection point, the chemical or biological agent could be injected into the water without destruction by any residual disinfectant. Without a remote water quality monitoring system in place with sensors in the distribution system, such contamination could go undetected for quite some time, allowing a thorough infiltration of a biological or chemical agent throughout the distribution system. By contrast, the remote water quality monitoring system could detect that the residual chlorine at the sensor had diminished to zero and sound the alarm. Especially with historical data available for comparison, the remote water quality monitoring system would be able to reduce the incidence of false terrorist attack alarms because data obtained from sensors at the treatment facility and in the distribution system could be compared. For example, a chlorine-dosing equipment failure might be determined and distinguished from a terrorist attack if a decrease in chlorine concentration is observed at both the water treatment plant and at points in the distribution system.

In the claims, unless specified otherwise, steps of a method may be performed in any order. For example, in a method claim, step (b) may be performed before step (a), unless the language of the claim requires that step (a) be performed prior to step (b).

Having described many embodiments of the present invention, it will be apparent that modifications, variations, alterations and changes are possible without departing from the full scope of the invention as defined in the appended claims, and equivalents thereof. It should be appreciated that all examples in the present disclosure, while illustrating many embodiments of the invention, are provided as non-limiting examples and are, therefore, not to be taken as limiting the various aspects so illustrated.

What is claimed is:

1. An apparatus comprising:
   one or more environmental instruments for collecting water quality data,
   a communication server for communicating with the environmental instruments,
   a call interval modifying module in communication with a logger for automatically changing a call interval for each environmental instrument of the one or more environmental instruments based on the collected water quality data and an environmental condition threshold value for the environmental instrument,
   wherein said call interval modifying module:
     determines that a first water quality measurement of an environmental instrument exceeds a threshold value;
     switches a primary call interval to a secondary call interval for the environmental instrument responsive to determining the first water quality measurement exceeds the threshold value;
     determines, while the environmental instrument operates according to the secondary call interval, that a second water quality measurement of the environmental instrument does not exceed the threshold value; and
     switches the secondary call interval to the primary call interval for the environmental instrument responsive to determining the second water quality measurement does not exceed the threshold value; and
   a web server for displaying on a visual display device the status of the one or more environmental instruments and/or the collected water quality data to a user,
   wherein the web server is in communication with the communication server and the visual display device.

2. The apparatus of claim 1, wherein the apparatus comprises a database server for storing the water quality data and wherein the database server is in communication with the communication server and the web server.

3. The apparatus of claim 1, wherein one or more environmental instruments comprise a logger.

4. The apparatus of claim 1, wherein one or more environmental instruments comprise a sampler.

5. The apparatus of claim 1, wherein the web server displays the collected water quality data on the visual display device.

6. The apparatus of claim 1, wherein the call interval modifying module comprises an instrument status-based call modifying module for changing the call interval for each of the one or more environmental instruments based on an environmental instrument status and an environmental instrument status threshold value for the environmental instrument.

7. The apparatus of claim 1, wherein the web server displays the environmental status for the environmental instrument on the visual display device.

8. The apparatus of claim 1, wherein the water quality data comprises water level data.

9. The apparatus of claim 1, wherein the water quality data comprises water flow data.

10. The apparatus claim 1, wherein the water quality data comprises water velocity data.

11. The apparatus of claim 1, wherein the apparatus comprises the visual display device.

12. The apparatus of claim 1, wherein the visual display device comprises at least a part of the call interval modifying module.

13. The apparatus of claim 1, wherein the environmental instruments are in wireless communication with the communication server.

14. The apparatus of claim 1, wherein the web server is in wireless communication with the one or more visual display devices.

15. A method comprising the following steps:
   (a) providing water quality data collected by one or more environmental instruments, and
   (b) changing a call interval for a selected environmental instrument of the one or more environmental instruments automatically based on the collected water quality data;

said changing comprising:
  determining, with a call interval modifying module in communication with a logger, that a first water quality measurement of an environmental instrument exceeds a threshold value;
  switching, with the call interval modifying module, a primary call interval to a secondary call interval for the environmental instrument responsive to determining the first water quality measurement exceeds the threshold value;
  determining, with the call interval modifying module and while the environmental instrument operates according to the secondary call interval, that a second water quality measurement of the environmental instrument does not exceed the threshold value; and
  switching, with the call interval modifying module, the secondary call interval to the primary call interval for the environmental instrument responsive to determining the second water quality measurement does not exceed the threshold value.

16. The method of claim 15, wherein the method comprises the following step:
  (c) displaying the collected water quality data to a user.

17. The method of claim 16, wherein step (c) comprises the user changing a call interval for the selected environmental instrument.

18. The method of claim 15, wherein the method comprises the following steps:
  (c) the one or more environmental instruments sending the collected water quality data to a communication server, and
  wherein step (b) is performed by the selected environmental instrument based on information received from the communication server.

19. An apparatus comprising:
  one or more environmental instruments for collecting water quality data,
  a communication server for communicating with the environmental instruments,
  an instrument status-based call modifying module in communication with a logger for automatically changing a call interval for each of the one or more environmental instruments based on an environmental instrument status and an environmental instrument status threshold value for the environmental instrument,
  wherein said call modifying module:
    determines that a first water quality measurement of an environmental instrument exceeds a threshold value;
    switches a primary call interval to a secondary call interval for the environmental instrument responsive to determining the first water quality measurement exceeds the threshold value;
    determines, while the environmental instrument operates according to the secondary call interval, that a second water quality measurement of the environmental instrument does not exceed the threshold value; and
    switches the secondary call interval to the primary call interval for the environmental instrument responsive to determining the second water quality measurement does not exceed the threshold value; and
  a web server for displaying on a visual display device the status of the one or more environmental instruments and/or the collected water quality data to a user,
  wherein the web server is in communication with the communication server and the visual display device.

20. The apparatus of claim 19, wherein the apparatus comprises a database server for storing the water quality data and wherein the database server is in communication with the communication server and the web server.

21. The apparatus of claim 19, wherein one or more environmental instruments comprise a logger.

22. The apparatus of claim 19, wherein one or more environmental instruments comprise a sampler.

23. The apparatus of claim 19, wherein the web server displays the collected water quality data on the visual display device.

24. The apparatus of claim 19, wherein the water quality data comprises water level data.

25. The apparatus of claim 19, wherein the water quality data comprises water flow data.

26. The apparatus of claim 19, wherein the water quality data comprises water velocity data.

27. The apparatus of claim 19, wherein the apparatus comprises the visual display device.

28. The apparatus of claim 19, wherein the visual display device comprises at least a part of the instrument status-based call modifying module.

29. The apparatus of claim 19, wherein the environmental instruments are in wireless communication with the communication server.

30. The apparatus of claim 19, wherein the web server is in wireless communication with the one or more visual display devices.

31. A method comprising the following steps:
  (a) one or more environmental instruments sending collected water quality data to a communication server at a frequency based on a first call interval, and
  (b) changing a selected environmental instrument of the one or more environmental instruments from a first call interval to a second call interval automatically based on a status of the selected environmental instrument,
  said changing comprising:
    determining, with a call interval modifying module in communication with a logger, that a first water quality measurement of an environmental instrument exceeds a threshold value;
    switching, with the call interval modifying module, a primary call interval to a secondary call interval for the environmental instrument responsive to determining the first water quality measurement exceeds the threshold value;
    determining, with the call interval modifying module and while the environmental instrument operates according to the secondary call interval, that a second water quality measurement of the environmental instrument does not exceed the threshold value; and
    switching, with the call interval modifying module, the secondary call interval to the primary call interval for the environmental instrument responsive to determining the second water quality measurement does not exceed the threshold value.

32. The method of claim 31, wherein the method comprises the following step:
  (c) displaying the status of the selected environmental instrument to a user.

33. The method of claim 32, wherein step (c) comprises the user changing a call interval for the selected environmental instrument of the one or more environmental instruments.

* * * * *